United States Patent [19]

Dzau et al.

[11] Patent Number: 5,631,237

[45] Date of Patent: May 20, 1997

[54] METHOD FOR PRODUCING IN VIVO DELIVERY OF THERAPEUTIC AGENTS VIA LIPOSOMES

[76] Inventors: Victor J. Dzau, 12101 Dawn La., Los Altos Hills, Calif. 94022; Yasufumi Kaneda, Molecular & Cellular Institute, Osaka University, 1-3, Yamada-oka, Suita-City, Osaka 565, Japan

[21] Appl. No.: 241,372

[22] Filed: May 10, 1994

Related U.S. Application Data

[63] Continuation-in-part of Ser. No. 995,022, Dec. 22, 1992, abandoned.

[51] Int. Cl.$^6$ .......................... A61K 48/00; A61K 9/127
[52] U.S. Cl. .......................... 514/44; 424/450; 424/417; 428/402.2; 264/4.1; 264/4.3; 264/4.6
[58] Field of Search .......................... 514/44, 2; 424/93.1, 424/450, 283.1, 1.21, 1.25; 435/320.1, 69.1, 5, 193

[56] References Cited

U.S. PATENT DOCUMENTS

| 4,377,567 | 3/1983 | Geho | 424/1.21 |
| 4,663,161 | 5/1987 | Mannino et al. | 424/450 |
| 5,077,211 | 12/1991 | Yarosh et al. | 435/193 |
| 5,264,618 | 11/1993 | Felgner et al. | 560/224 |

OTHER PUBLICATIONS

Uchida, Exp. Cell Res., 178, 1988, 1–17.
Volsky et al, FEBS letters, 92(2), 1978, 190–194.
Stewart et al, Hum. Gene Ther., 3, 1992, 267–275.
Maruyama et al, ANAS, 87 1990, 5744–5748.
Uhlmann et al, Chem. Reviews, 90(4), 1990, 544–584.
Okada, 1958, Biken's J. 1: 103–110, "The Fusion of Ehrlich's Tumor Cells caused by HVJ Virus in vitro".
Okada, 1962, Exp. Cell Res. 26: 98–107, "Analysis Of Giant Polynuclear Cell Formation Caused By HVJ Virus From Ehrlich's Ascites Tumor Cells – I. Microscopic Observation Of Giant Polynuclear Cell Formation".
Okada and Tadokoro, 1962, Exp. Cell Res. 26: 108–118, "Analysis Of Giant Polynuclear Cell Formation Caused By HVJ Virus From Ehrlich's Ascites Tumor Cells – II. Quantitative Analysis Of Giant Polynuclear Cell Formation".
Okada, 1962, Exp. Cell Res. 26: 119–128. "Analysis Of Giant Polynuclear Cell Formation Caused by HVJ Virus From Ehrlich's Ascites Tumor Cells – III. Relationship Between Cell Condition And Fusion Reaction Or Cell Degeneration Reaction".
Furusawa and Nishimura, 1974, Nature 249: 449–450, "Injection of foreign substances into single cells by cell fusion".
Okada et al., 1975, Exp. Cell. Res. 93: 368–378, "Modification Of Cell Membranes With Viral Envelopes During Fusion Of Cells With HVJ (Sendai Virus) – I. *Interaction between Cell Membranes and Virus in the Early Stage*".
Uchida et al., 1979, J. Cell. Biol. 80: 10–20, "Reconstitution Of Lipid Vesicles Associated With HVJ (Sendai Virus) Spikes – Purification and Some Properties of Vesicles Containing Nontoxic Fragment A of Diphtheria Toxin".

Uchida et al., 1979, Biochem. Biophys. Res. Comm. 87: 371–379, "Improved Methods Using HVJ (Sendai virus) For Introducing Substances Into Cells".
Yamaizumi et al., 1979, Virology 95: 218–221, "Macromolecules Can Penetrate the Host Cell Membrane during the Early Period of Incubation with HVJ (Sendai Virus)".
Yoshima et al., 1981, J. Biol. Chem. 256: 5355–5361, "Carbohydrate Structures of HVJ (Sendai Virus) Glycoproteins".
Miura et al., 1982, Exp. Cell Res. 141: 409–420, "HVJ (Sendai Virus)–Induced Envelope Fusion And Cell Fusion Are Blocked by Monoclonal Anti–HN Protein Antibody That Does Not Inhibit Hemagglutination Activity of HVJ".
Nakanishi et al., 1982, Exp. Cell Res. 142: 95–101, "Glycoproteins Of Sendai Virus (HVJ) Have A Critical Ratio For Fusion Between Virus Envelopes And Cell Membranes".
Uchida et al., 1984, Exp. Cell Res. 152: 313–321, "HN Glycoprotein of HVJ (Sendai Virus) Enhances the Selective Cytotoxicity of Diphtheria Toxin Fragment A–containing Liposomes on Subacute Sclerosing Panencephalitis Virus–infected Cells".
Miura et al., 1985, FEBS Letter 188: 112–116, "Molecular cloning of a full–length cDNA encoding the hemagglutinin–neuraminidase glycoprotein of Sendai virus".
Miura et al., 1985, Gene 38: 271–274, "Use of the deoxyinosine–containing probe to isolate and sequence cDNA encoding the fusion (F) glycoprotein of Sendai virus (HVJ)".
Nakanishi et al., 1985, Exp. Cell Res. 159: 399–409, "Efficient Introduction of Contents of Liposomes into Cells using HVJ (Sendai Virus)".
Kaneda et al., 1987, Exp. Cell Res. 173: 56–69, "The Improved Efficient Method for Introducing Macromolecules into Cells Using HVJ (Sendai Virus) Liposomes with Gangliosides".
Uchida, 1988, Exp. Cell. Res. 178: 1–17, "Introduction of Macromolecules into Mammalian Cells by Cell Fusion".
Kaneda et al., 1989, Science 243: 375–378, "Increased Expression of DNA Cointroduced with Nuclear Protein in Adult Rat Liver".

(List continued on next page.)

*Primary Examiner*—Jacqueline M. Stone
*Assistant Examiner*—Andrew Milne
*Attorney, Agent, or Firm*—Flehr, Hohbach, Test, Albritton & Herbert

[57] ABSTRACT

Methods and compositions are provided for intracellular transfer of a wide variety of agents, by using Sendai virus comprising liposomes having various compositions in the liposome lumen. A preferred method for preparing the liposomes provides for enhanced levels of luminal concentrations, as well as incorporation of high molecular weight molecules. The method comprises fusing liposomes, where one liposome comprises the Sendai virus proteins and the other liposome comprises the luminal composition. The subject methods find particular application with intranuclear transfer of nucleic acids, more particularly with cells of the vasculature.

10 Claims, 18 Drawing Sheets

OTHER PUBLICATIONS

Kaneda et al., 1989, J. Biol. Chem. 264: 12126–12129, "Introduction and Expression of the Human Insulin Gene in Adult Rat Liver".

Kato et al., 1991, J. Biol. Chem. 266: 3361–3364, "Expression of Hepatitis B Virus Surface Antigen in Adult Rat Liver".

Kato et al., 1991, J. Biol. Chem. 266: 22071–22074, "Direct Injection of Hepatitis B Virus DNA into Liver Induced Hepatitis in Adult Rats".

Tomita et al., 1992, Biochem. Biophys. Res. Comm. 186: 129–134, "Direct In Vivo Gene Introduction Into Rat Kidney".

Tomita et al., 1991, American Heart Association, Council for High Blood Pressure Research, 45th Annual Fall Conference and Scientific Session, Chicago, IL (Abstract), "Efficient and Selective Gene Introduction Method Into Glomerular Cells Of Rat Kidney".

Tomita et al., 1992, J. Hypertension 10: S13 (Abstract No. P28), "Direct In Vivo Gene Introduction Of Human Renin Into The Rat".

Nabel et al., 1989, Science, 244: 1342–1344, "Recombinant Gene Expression in Vivo Within Endothelial Cells of the Arterial Wall".

Wilson et al., 1989, Science 244: 1344–1346, "Implantation of Vascular Grafts Lined with Genetically Modified Endothelial Cells".

Dichek et al., 1989, Circulation 80: 1347–1353, "Seeding of Intravascular Stents With Genetically Engineered Endothelial Cells".

Swain, 1989, Circulation 80: 1495–1496, "Gene Therapy: A New Approach to the Treatment of Cardiovascular Disease".

Nabel et al., 1990, Science 249: 1285–1288, "Site-Specific Gene Expression in Vivo by Direct Gene Transfer into the Arterial Wall".

Moullier et al., 1991, Nouv. Rev. Fr. Hematol. 33: 493–495, "Gene transfer to somatic tissues using retroviral vectors".

Lim et al., 1991, Circulation 83: 2007–2011, "Direct In Vivo Gene Transfer Into the Coronary and Peripheral Vasculatures of the Intact Dog".

Flugelman et al., 1991, Circulation 85: 1110–1117, "Low Level In Vivo Gene Transfer Into the Arterial Wall Through a Perforated Balloon Catheter".

Meidell et al., 1991, Circulation 85: 1219–1220, "The End of the Beginning – Gene Transfer Into the Vessel Wall".

Nabel et al., 1991, J. Amer. College Cardiology 17: 189B–194B, "Gene Transfer Into Vascular Cells".

Felgner and Rhodes, 1991, Nature 349: 351–352, "Gene therapeutics".

Nabel and Nabel, 1991, Trends in Cardiovascular Medicine Jan./Feb.: 12–17, "Gene Transfer and Cardiovascular Disease".

Crystal, 1992, Amer. J. Med. 92(supp.6A): 44S–52S, "Gene Therapy Strategies for Pulmonary Disease".

Lynch et al., 1992, Proc. Natl. Acad. Sci. USA 89: 1138–1142, "Long-term expression of human adenosine deaminase in vascular smooth muscle cells of rats: A model for gene therapy".

Roemer and Friedmann, 1992, Eur. J. Biochem. 208: 211–225, "Concepts and strategies for human gene therapy".

Karson et al., 1992, J. Repro. Med. 37:508–514, "Prospects for Human Gene Therapy".

Cometta, 1992, Brit. J. Haematol. 80: 421–426, "Annotation–Safety Aspects Of Gene Therapy".

Hazinski, 1992, Sem. Perinatol. 16: 200–204, "Liposome–Mediated Transfer of Fusion Genes to the Intact Lung".

Simons et al., 1992, Nature 359: 67–70, "Antisense c–myb oligonucleotides inhibit intimal arterial smooth muscle cell accumulation in vivo".

Chapman et al., 1992, Circulation Res.,71: 27–33, "Gene Transfer Into Coronary Arteries of Intact Animals With a Percutaneous Balloon Catheter".

Merrouche and Favrot, 1992, Human Gene Therapy 3: 285–291, "Retroviral Gene Therapy and Its Application in Oncohematology".

Tolstoshev, 1992, Bone Marr. Trans. (GB) 9(suppl.1): 148–150, "Retroviral–mediated gene therapy – safety considerations and preclinical studies".

Dzau et al., 1992, VIIth International Symposium on the Biology of Vascular Cells, San Diego, California (Nov. 10–14, 1992), "Molecular Inhibition of Vascular Smooth Muscle Proliferation Using Antisense Oligonucleotide: Therapy for Restenosis".

Morishita et al., 1992, American Heart Association, Council for High Blood Pressure Research, 46th Annual Fall Conference and Scientific Sessions, Hypertension 20(3): 441 (Abstract 316), "Novel Gene Transfer Method For Study Of Vascular Renin–Angiotensin System (RAS)".

Keown et al., 1990, Methods in Enzymology, 185: 527–537, "Methods for Introducing DNA into Mammalian Cells".

Morishita et al., 1993, J. Am. Coll. Cardiol. 21:74A, "In vivo transfer of antisense cell cycle genes using HVJ method prevents neointimal hyperplasia in balloon–injured rat carotid artery".

Kaneda et al., 1984, J. Cell Biol. 98: 466–472, "Entry of Diphtheria Toxin into Cells: Possible Existence of Cellular Factor(s) for Entry of Diphtheria Toxin into Cells Was Studied in Somatic Cell Hybrids and Hybrid Toxins".

UNINJURED CONTROL

INJURED SENSE

INJURED CONTROL

INJURED ANTISENSE

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GGCTGCCATG GTCCC                                                15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GGGACCATGG CAGCC                                                15

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TAGAACTCTT GCTTGCTTTG CTA                                23

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CATTGCATAC TCTGTTACAA GCT                                23

( 2 ) INFORMATION FOR SEQ ID NO:5:

( i ) SEQUENCE CHARACTERISTICS:

( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:5:

TTGTAACCAA CTGGGACGAT ATGG 24

( 2 ) INFORMATION FOR SEQ ID NO:6:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:6:

GATCTTGATC TTCATGGTGC TAGG 24

( 2 ) INFORMATION FOR SEQ ID NO:7:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:7:

GCCUCCCCA UGCCGCCUC CGGG 24

( 2 ) INFORMATION FOR SEQ ID NO:8:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:8:

GGAGGGCGGC ATGGG 15

( 2 ) INFORMATION FOR SEQ ID NO:9:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:9:

CCCATGCCGC CCTCC 15

( 2 ) INFORMATION FOR SEQ ID NO:10:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:10:

GGGTACGGCG GGAGG 15

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GCAGGGACCA UGGCAGCCGG GAGC 24

( 2 ) INFORMATION FOR SEQ ID NO:12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GGCTGCCATG GTCCC 15

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GGGACCATGG CAGCC 15

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CCCTGGTACC GTCGG 15

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CGGGACGCGA UGAGGACCUU GGCU 24

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

AGCCAAGGTC CTCAT                    15

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

ATGAGGACCT TGGCT                    15

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

UGAGUAACUA UGGAAGACUA UAUC          24

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

GTCTTCCATA GTTACTCA                18

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

TGAGTAACTA TGGAAGAC                18

( 2 ) INFORMATION FOR SEQ ID NO:21:

( i ) SEQUENCE CHARACTERISTICS:

( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

AACUCCGCCA CCAUGUUUGA GGCACGCCUG                30

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

GATCAGGCGT GCCTCAAA                             18

( 2 ) INFORMATION FOR SEQ ID NO:23:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

CTCAAACATG GTGGC                                15

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

TTTGAGGCAC GCCTGATC                             18

( 2 ) INFORMATION FOR SEQ ID NO:25:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

GCCACCATGT TTGAG                                15

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:26:

UGGCGCUUCA UGGAGAACUU CCAA  24

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:27:

GAAGTTCTCC ATGAAGCG  18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:28:

CGCTTCATGG AGAACTTC  18

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:29:

GGAGGAGCCA UGGCGCUCAG GGGU  24

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:30:

CCTGAGCGCC ATGGCTCC  18

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:31:

GGAGGCATGG CGCTCAGG  18

( 2 ) INFORMATION FOR SEQ ID NO:32:

( i ) SEQUENCE CHARACTERISTICS:
       ( A ) LENGTH: 16 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:32:

ACCGCGCCAU GGGGGC                      16

( 2 ) INFORMATION FOR SEQ ID NO:33:

( i ) SEQUENCE CHARACTERISTICS:
       ( A ) LENGTH: 16 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:33:

GCCCCCATGG CGCGGT                      16

( 2 ) INFORMATION FOR SEQ ID NO:34:

( i ) SEQUENCE CHARACTERISTICS:
       ( A ) LENGTH: 16 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:34:

ACCGCGCCAT GGGGCC                      16

METHOD FOR PRODUCING IN VIVO DELIVERY OF THERAPEUTIC AGENTS VIA LIPOSOMES

CROSS-REFERENCE TO RELATED APPLICATIONS

This application is a continuation-in-part of Ser. No. 07/995,022, filed Dec. 22, 1992 (now abandoned).

INTRODUCTION

1. Technical Field

The field of this invention relates to in vivo intracellular delivery of compositions.

2. Background

In the course of normal deterioration, traumatic injury, or disease induced degradation, a living organism will suffer damage to a variety of tissues through the course of its existence. Normally the natural regenerative powers of the organism will allow for partial or complete recovery from such sustained damage, but there are times when the organism cannot repair the damaged tissues, either due to congenital defect, extent of the damage, or the nature of the disease. Timely intervention in many cases may correct damage, prevent permanent damage, or even prevent failure of the tissue. This intervention may thus improve the quality of life, or even prolong the life of the organism.

One area of concern is vascular disease, which affects a large segment of the human population where the leading cause of death is due to ischemic heart disease, with 217.4 deaths per 100,000 people (National Center for Health Statistics, Vital Statistics Report, Vol. 35, Aug. 24, 1987 in Professional Guide to Diseases, Springhouse Corp. 3rd ed. 1989). Present methods of treatment are focused on education about lifestyle, exercise, and diet with the aim of preventing, or delaying many cardiovascular problems. More immediate treatments, in the case of acute failure of components of the cardiovascular system, involve treating the vessels to remove damaged portions surgically, or by treating damaged portions with balloon angioplasty to improve the performance of damaged tissues. During the course of balloon angioplasty, physical damage to the blood vessels is often a critical side effect of the treatment which results in restenosis. Other procedures lead to vessel trauma as well, for example vein bypass graft stenosis, prosthetic graft stenosis, and damage from other procedures. There are also several systemic-physiological problems that can lead to degradation of the cardiovascular system, among these are atherosclerosis, hypertension, angiogenesis, myocardial hypertrophy, and vascular smooth muscle cell (VSMC) hypertrophy. For example, in the case of chronic hypertension, it is thought that multiple factors play a role in determining susceptibility and degree of the problem. While all of the physiological factors that may contribute to chronic hypertension are unknown, it is believed that the resulting damage to the blood vessels eventually contributes to future cardiovascular failure.

Research on the vascular response to injury reveals that it involves alteration of several cellular processes: cell growth, cell migration and extracellular matrix production. This vascular response to injury is characteristic of the pathogenesis of various vascular diseases. For example, atherosclerotic lesions evolve as a result of vascular smooth muscle migration into the subintimal space, proliferation and the production of abundant extracellular matrix. In similar fashion, restenosis after angioplasty, vein bypass graft stenosis, prosthetic graft stenosis, angiogenesis and hypertension all involve abnormalities in vascular cell growth, migration and matrix composition. The precise mechanisms responsible for alterations in the regulation of these cellular processes are poorly characterized. Experimental studies suggest that changes in the expression of autocrine/paracrine growth factors by vascular cells and/or autocrine/paracrine growth factors produced by blood borne cells that adhere and/or invade the vessel wall play an important pathogenic role in vascular damage and lesion formation.

Besides vascular diseases, numerous other organs suffer from a wide variety of diseases where intracellular administration could be beneficial. Thus, treatments of such organs as kidney, heart, liver, spleen, gut, pancreas, and the like, where one could deliver intracellularly therapeutic compositions, using either invasive or non-invasive modalities, would be of substantial interest. While many methodologies are available for introducing various compositions, particularly DNA, into cells, these techniques are, for the most part, restricted to in vitro applications and are not adaptable to in vivo applications. While liposomes comprising Sendai virus have been employed for introduction of DNA into the reticuloendothelial system, the use of this approach has not been shown for distinctively different types of cells or for organs unassociated with the reticuloendothelial system.

RELAVANT LITERATURE

In a series of reports from Japan, the egg-adapted Z strain of Hemagglutinating Virus of Japan (HVJ), a Sendai virus, has been described as a cell fusion agent and used with liposomes for delivery of various substances into cells. These reports, briefly summarized, are as follows.

Okada, 1958, Biken's J. 1:103–110, discloses fusion of Ehrlich's tumor cells caused by HVJ virus in vitro.

Okada, 1962, Exp. Cell Res. 26:98–107, discloses microscopic observation of giant polynuclear cell formation caused by HVJ virus from Ehrlich's ascites tumor cells.

Okada and Tadokoro, 1962, Exp. Cell Res. 26:108–118, discloses the quantitative analysis of giant polynuclear cell formation caused by HVJ virus from Ehrlich's ascites tumor cells.

Okada, 1962, Exp. Cell Res. 26:119–128, discloses the relationship between cell condition and fusion reaction or cell degeneration reaction of giant polynuclear cells caused by HVJ virus from Ehrlich's ascites tumor cells.

Furusawa and Nishimura, 1974, Nature 249:449–450, discloses the injection of foreign substances using erythrocyte ghosts into FL cells coated with HVJ.

Okada, et al., 1975, Exp. Cell. Res. 93:368–378, discloses the modification of cell membranes with viral envelopes during fusion of the cells with HVJ, and focuses on the interaction between cell membranes and virus in the early stage of the fusion process.

Uchida, et al., 1979, J. Cell. Biol. 80:10–20, discloses preparation of lipid vesicles associated with HVJ spikes.

Uchida, et al., 1979, Biochem. Biophys. Res. Comm. 87:371–379, discloses an improved method for introducing a substance into cells using HVJ by sonicating the HVJ virions in the presence of a protein (in this study, fragment A of diphtheria toxin) and using the HVJ-protein complex for cell fusion.

Yamaizumi, et al., 1979, Virology 95:218–221, discloses that fragment A of diphtheria toxin (MW 22,000) can penetrate the cell membrane during incubation with UV-inactivated HVJ.

Yoshima, et al., 1981, J. of Biochem. 256:5355–5361, discloses the carbohydrate structures of two membrane glycoproteins (HANA and F proteins) of HVJ.

Miura, et al., 1982, Exp. Cell Res. 141:409–420, discloses two monoclonal antibodies (Mab) against HN protein of HVJ; one Mab (HN-1) inhibited hemagglutination activity of HVJ, while the other Mab (HN-2) inhibited HVJ-induced fusion.

Nakanishi, et al., 1982, Exp. Cell Res. 141:95–101, discloses that when the ratio of the F to HN glycoproteins of HVJ is 2, there is optimal fusion as measured by the cytotoxic activity of reconstituted F-HN-lipid vesicles containing fragment A of diphtheria toxin that are fused with L cells.

Uchida, et al., 1984, Exp. Cell Res. 151:313–321, discloses that liposomes associated with HN which contain fragment A of diphtheria toxin were more cytotoxic than naked liposomes without HN but which contain fragment A on subacute sclerosing panencephalitis virus-infected cells.

Miura, et al., 1985, FEBS Letter 188:112–116, discloses the molecular cloning of a full-length cDNA encoding the hemagglutinin-neuraminidase (HN) glycoprotein of HVJ.

Miura, et al., 1985, Gene 38:271–274, discloses the isolation and sequence of the cDNA encoding the fusion (F) glycoprotein of HVJ.

Nakanishi, et al., 1985, Exp. Cell Res. 159:399–409, discloses the introduction of the contents of liposomes containing fragment A of diphtheria toxin (DA) into cells treated with HVJ; DA-liposomes preincubated with HVJ were also toxic to cells.

Kaneda, et al., 1987, Exp. Cell Res. 173:56–69, teaches an improved method for introducing certain DNA and RNA macromolecules into cells using HVJ-liposomes with gangliosides.

Uchida, 1988, Exp. Cell. Res. 178:1–17, is a review of methods of introduction of macromolecules (DNA, RNA or protein) into mammalian cells by cell fusion using erythrocyte membranes or liposomes treated with HVJ or glycoprotein (HN and F).

Kaneda, et al., 1989, Science 243:375–378, discloses a two vesicle system for the increased expression of DNA cointroduced with nuclear protein (HMG-1) via (i) HVJ-liposome complexes loaded with DNA that had been incubated with (ii) RBC membrane complexes containing HMG1 protein in adult rat liver by injection of the complexes into the portal vein.

Kaneda, et al., 1989, J. Biol. Chem. 264:12126–12129, discloses the use of their previously described two vesicle system for the introduction and expression of the human insulin gene in adult rat liver via injection into the portal vein of (i) HVJ-liposome-ganglioside complexes loaded with the human insulin gene that had been incubated with (ii) RBC membrane complexes containing HMG-1 protein.

Kato, et al., 1991, J. Biol. Chem. 266:3316–3364, discloses a single vesicle system for the introduction and expression of the hepatitis B virus surface antigen gene via HVJ-liposome complexes with HMG-1 injected under the perisplanchnic membrane of adult rat liver.

Kato, et al., 1991, J. Biol. Chem. 266:22071–22074, discloses the introduction and expression of hepatitis B virus surface antigen genes into adult rat liver resulting in hepatitis, via HVJ-liposome complexes with HMG-1 injected under the perisplanchnic membrane of adult rat liver.

Tomita, 1992, Biochem. Biophys. Res. Comm. 186:129–134, discloses the introduction and expression of a reporter gene into rat kidney via HVJ-liposomes encapsulating DNA and HMG1 injected through a canula in the renal artery.

Tomita, et al., 1992, J. Hypertension 10:513, Abstract No. P28, discloses the introduction and expression of the human renin gene via HVJ-liposomes injected under the perisplanchnic membrane of rat liver.

A number of reports describe, comment upon or summarize recent gene transfer experiments in which retroviral-mediated or liposomal (neutral or cationic) mediated transfer methods were used, including the following reports, briefly summarized.

Nabel, et al., 1989, Science, 244:1342–1344 discloses the re-introduction in vivo of endothelial cells from the Yucatan minipig that had been transfected in vitro with a replication defective retroviral vector encoding galactosidase into the arterial wall of the pig by means of a specially designed arterial catheter after mechanical denuding of the arterial wall via balloon catheter.

Wilson, et al., 1989, Science 244:1344–1346, discloses the implantation in vivo of prosthetic vascular grafts lined with previously harvested vascular endothelial cells from mongrel dogs that had been transfected in vitro with a replication-defective retrovirus encoding β-galactosidase via surgical implantation as carotid interposition grafts in the dogs.

Dichek, et al., 1989, Circulation 80:1347–1353, discloses (i) the seeding of stainless steel intravascular stents with endothelial cells transfected in vitro with a replication-defective retrovirus encoding either galactosidase or tissue plasminogen activator and (ii) the expansion of the stents in vitro with balloon catheters for the examination of cell retention on the stent surfaces.

Swain, 1989, Circulation 80:1495–1496, is an editorial comment on gene therapy as a promising new approach to the treatment of cardiovascular disease using genetically engineered endothelial cells coating intravascular stents as reported by the above-listed Nabel, Wilson and Dichek publications.

Nabel, et al., 1990, Science 249:1285–1288, discloses the expression of a β-galactosidase gene in a specific arterial segment in vivo in Yucatan pigs by direct infection with a murine amphotropic retroviral vector or by DNA transfection with the use of cationic liposomes.

Moullier, et al., 1991, Nouv. Rev. Fr. Hematol. 33:493–495, discloses gene transfer using retroviral vectors (i) to skin fibroblasts transfected in vitro and implanted in organoids in vivo, (ii) to bone marrow cells co-cultivated with fibroblasts producing the recombinant retrovirus and used to reconstitute lethally irradiated mice, and (iii) to hepatocytes via perfusion of a high titer suspension of retroviral vector through a canula inserted in the portal vein of two-third hepatectomized rats.

Lim, et al., 1991, Circulation 83:2007–2011, discloses in vivo gene transfer of reporter genes (β-galactosidase and luciferase) via cationic liposomes into the coronary and femoral arteries of dogs; luciferase, but not β-galactosidase, was found to be a reliable marker in the dog model.

Flugelman, et al., 1991, Circulation 85:1110–1117, discloses low level or undetectable in vivo gene transfer into the arterial wall using retroviral vector-containing virions injected through a perforated balloon catheter; there was no detectable expression of the transferred genes.

Meidell, et al., 1991, Circulation 85:1219–1220, is an editorial comment on experimental results to date of gene transfer into the vessel wall, including a summary of and commentary on Flugelman et al.'s results showing no expression of foreign genes introduced via several retroviral constructs.

Nabel, et al., 1991, J. Amer. Coll. Card. 17:189B–194B, is a review focusing on attempts to target genes to cells and tissues relevant to cardiovascular disorders.

Felgner and Rhodes, 1991, Nature 349:351–352, is a brief review of gene therapeutics for the direct delivery of purified genes in vivo, without the use of retroviruses.

Nabel and Nabel, 1991, Trends in Cardiovascular Medicine Jan/Feb:12–17, is a brief review focusing on attempts to target gene modification to cardiovascular disorders, particularly diseases of the vasculature.

Crystal, R. G., 1992, Amer. J. Med. 92(supp.6A):44S–52S, describes general strategies of gene therapy for treating pulmonary disease.

Lynch, et al., 1992, Proc. Natl. Acad. Sci. USA 89:1138–1142, discloses that vascular smooth muscle cells of rats can be explanted, cultured and genetically modified using retroviral vectors in vitro, then returned to denuded vasculature for detection of gene expression; adenosine deaminase but not β-galactosidase was useful as a transferred marker gene; direct gene transfer by infusion of recombinant retrovirus into rat carotid arteries was not observed.

Roemer and Friedmann, 1992, Eur. J. Biochem. 208:211–225, is a review of some concepts and strategies for human gene therapy.

Karson et al., 1992, J. Repro. Med. 37:508–514, is an overview of research utilizing gene transfer to treat human genetic diseases and prospects for human gene therapy using retroviral vectors.

Cornetta, 1992, Brit. J. Haem. 80:421–426, is an annotation on safety aspects of gene therapy using retroviral vectors.

Hazinski, 1992, Sem. Perinatol. 16:200–204, discloses cationic liposome-mediated transfer of fusion reporter genes to the lung epithelial cells and transient protein expression via direct injection of DNA-liposome solution into the trachea.

Simons, et al., 1992, Nature 359:67–70, discloses a rat carotid injury model for the local delivery of a gelling solution of antisense c-myb oligonucleotides to the outside of the isolated carotid artery from which the adventitia was stripped immediately after balloon angioplasty to denude the endothelium; the result was the inhibition of intimal arterial smooth muscle cell accumulation in vivo.

Chapman, et al., 1992, Circulation Res., 71:27–33, discloses transfer of the luciferase reporter gene into coronary arteries of intact dogs with a percutaneous balloon catheter using cationic liposome-DNA complexes or DNA alone for transfer.

Merrouche and Favrot, 1992, Human Gene Therapy 3:285–291, summarize a symposium on feotal and neonatal cell transplantation and retroviral gene therapy.

Tolstoshev, 1992, Bone Marr. Trans. (GB) 9(sup.1):148–150, is a review of the research of the author and his collaborators related to retroviral-mediated gene therapy and safety considerations of clinical use of retroviral vectors.

Many complications are involved with treating the vasculature in vivo. Despite significant efforts by many research laboratories, the demand for an efficient, safe method for delivery of therapeutic agents to cells of the vasculature, in particular, intraluminal delivery where only brief incubation periods are required to effect delivery of the agents, has not been satisfied by methods of retroviral-mediated transfer or liposomal (neutral or cationic) mediated transfer.

Recently, our laboratory has developed a method for in vivo gene transfer to cells of the vasculature that does not involve the use of retroviral vectors or cationic liposomes for transfer, as indicated in the following briefly summarized abstracts.

Dzau, et al., 1992, International Symposium on the Biology of Vascular Cells, presented in San Diego, Calif. on Nov. 10–14, 1992, discloses results of the molecular inhibition of vascular smooth muscle proliferation using antisense oligonucleotides encapsulated in HVJ-liposomes as therapy for restenosis.

Morishita, et al., 1992, American Heart Association, Council for High Blood Pressure Research 42nd Annual Fall Conference and Scientific Sessions, (Circulation 86:1–227, abstract no. 902) discloses results of a novel gene transfer method using HVJ-liposomes for the study of the vascular renin-angiotensin system.

Morishita, et al., 1992, American Heart Association, 65th Scientific Sessions Abstract Form, (Hypertension 20(3):441, abstract no. 316) discloses results of in vivo gene transfer into intact blood vessels using HVJ-liposomes versus cationic liposomes for transfer.

SUMMARY OF THE INVENTION

In accordance with the subject invention, methods and compositions are provided for intracellular delivery of compositions in vivo. The methods and compositions employ liposomes comprising Sendai virus proteins for efficient fusion of the liposomes to cell targets. Various compositions may be introduced into the lumen of the liposomes for intracellular delivery.

The method comprises providing for contact between the liposome and the target cells, where the contact may be as a result of isolation of a particular site or preferential contact between the liposomes and the target site. The liposomes fuse with the cells of the target site and deliver the contents of the lumen intracellularly. The liposomes may be maintained in contact with the cells for sufficient time for fusion, using various means to maintain contact, such as isolation, binding agents, and the like. Various compositions may be delivered, including nucleic acids, proteins, sugars, small naturally occurring or synthetic molecules, combinations thereof, and the like. The compositions may serve a wide variety of prophylactic or therapeutic purposes.

The liposome compositions which are employed may include one or more components which cooperate with a functional moiety employed for achieving a particular end. The additional components may serve as aiding transport to the nucleus, degradation of a nucleic acid target or integration into the host genome. For example, where the composition is a nucleic acid, for intranuclear delivery, the liposome may comprise a non-histone chromosomal high mobility group protein. Also, various modes of administration may be employed for delivery.

A preferred method of preparing the liposomes is provided comprising fusing liposomes, which have proteins from Sendai virus which enhance cellular fusion, with liposomes having the composition for intracellular delivery.

BRIEF DESCRIPTION OF THE DRAWINGS

FIG. 9A shows SV40 large T antigen cDNA transformed cells; FIG. 9B shows control vector transformed cells. Cross-sections of tissue were photographed at 100× magnification.

FIG. 10A shows SV40 large T antigen cDNA transformed cells; FIG. 10B shows control vector transformed cells. Cross-sections of tissue were photographed at 100 × magnification.

DESCRIPTION OF THE SPECIFIC EMBODIMENTS

Figure 1:
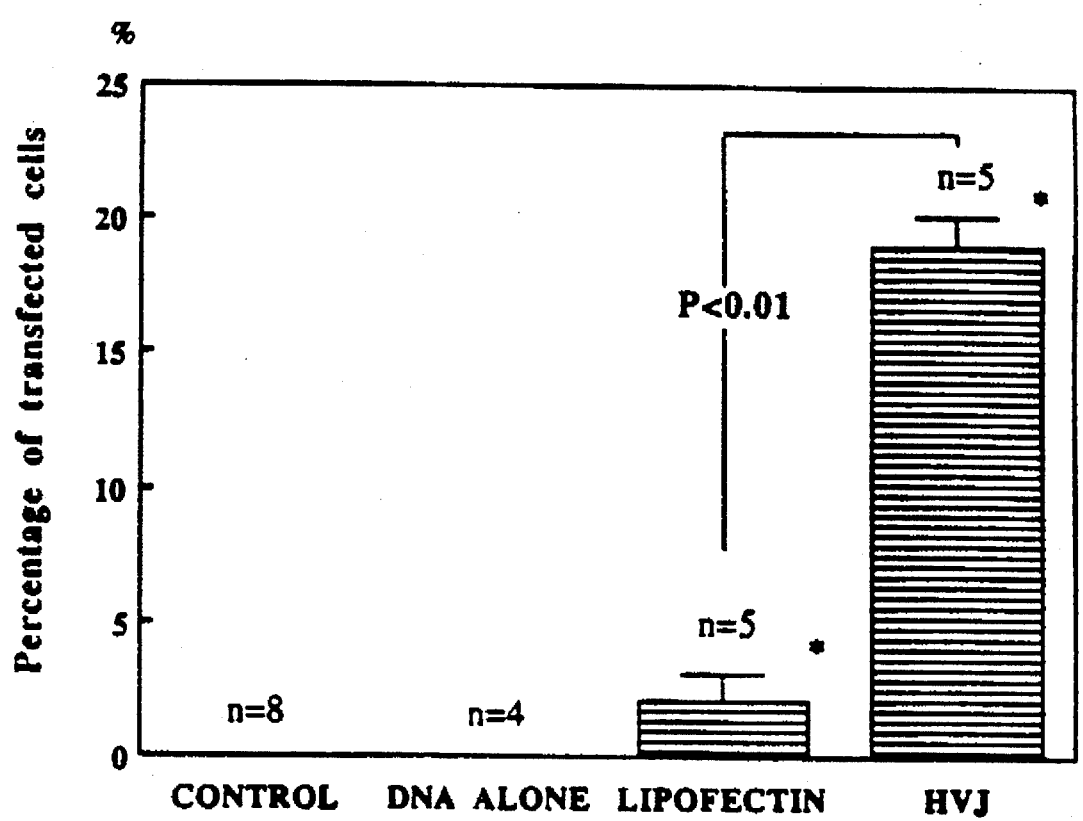
FIG. 1 is a bar graph illustrating the efficiency of transfection comparing the percentage of cells transfected with SV40 large T antigen via HVJ-liposomes, cationic liposomes (lipofectin) or DNA alone, as detected by immunohistochemical staining in vitro as described in Example 1.

The present invention provides methods for the delivery of one or more therapeutic agents via transfer vesicles to target cells in vivo, although the method may also be used ex vivo or in vitro (culture). The subject method involves delivering intracellularly compositions of interest for a wide variety of purposes, experimental, prophylactic and therapeutic. The methodology comprises preparing liposomes having Sendai virus (also referred to as Hemagglutinating Virus of Japan, hereinafter referred to as (HVJ)) proteins, to enhance cellular fusion, the composition of interest in the lumen of the liposome comprising one or more components. The Z strain of HVJ is preferred.

The method of administration of the liposomes to the target cells will depend upon the target cells, whether the administration is in vivo, ex vivo or in vitro, and the nature of the liposomes. Targeting may be as a result of preferential accumulation of the liposomes at a particular site or organ, isolation of the cellular target, vascular administration and homing as a result of binding affinity of a specific binding compound on the surface of the liposome, or the like.

A preferred method for preparing liposomes for improved delivery comprises preparing liposomes having purified F and HN polypeptides from HVJ and preparing stable liposomes, using appropriate lipids for liposome formation. By purified it is intended that the proteins of interest comprise at least 95 weight % of the proteins present in the composition, preferably at least about 99 weight % or more, where the ratio of the HN to F proteins will generally be in the range of about the natural range, ±50%. Conveniently, the protein composition comprising the HN and F proteins is combined with lyophilized lipids with a small amount of aqueous medium comprising a non-ionic detergent, followed by dialysis to remove the detergent. Various non-ionic detergents may be employed, such as NP-40, and equivalent detergents. The weight ratio of protein-to-lipid will generally be in the range of about 0.1–1:1, more usually from about 0.25–0.75:1. The lipids may be any useful combination of known liposome forming lipids, where at least about 25 number percent, preferably about 75 number percent, and not more than about 90 number percent will be cationic lipids, such as phosphatidyl choline. The remaining lipid will normally be neutral lipids, such as cholesterol, phosphatidyl serine, phosphatidyl glycerol, and the like. Preferably, at least about 5 mol percent and usually not more than about 20 mol percent of the lipid will be cholesterol, which provides for a more stable liposome as is known in the art. The detergent will generally be present in from about 0.1–2%, more usually about 0.5–1% in an aqueous medium, e.g. balanced saline of from about 5 to 500 mM, which medium may be buffered with conventional buffers, such as phosphate, carbonate, etc., generally at a concentration in the range of about 5–500 mM. The mixture may be agitated, conveniently sonicated to provide for liposomes, where the liposomes lacking the proteins may be separated from liposomes having incorporated proteins by employing various techniques, e.g. gel filtration. Desirably, the liposomes should have from about 3,000 to about 20,000 HAU (hemagglutinating unit) as determined by optical density at 540 nm. The liposomes may be stored at reduced temperatures, particularly 4° C. for about a week.

Separately, liposomes are prepared by combining the agent or composition of interest for delivery to the target cells in conjunction with the appropriate lipids, conveniently comprising the same lipids as previously used and may further include additional lipids, particularly neutral lipids, where the range of the ratios of the neutral lipids to the cationic lipids is different from the liposomes with the HVJ proteins. Particularly, the neutral to cationic lipids will generally be from about 0.2–1:1 mole ratio, more usually about 0.25–0.5:1 mole ratio. The weight ratio of the composition of interest to be delivered in relation to the lipid composition may be varied widely, but by use of the subject invention, higher levels of the subject compositions of interest can be provided in the lumen of the liposome. Particularly, the weight ratio will generally be about 1–500× $10^{-3}$:1, more usually about 1–50×$10^{-2}$:1 weight ratio.

Other components may also be present to fulfill particular functions. For example, for compositions for transport to the nucleus, nuclear proteins may be employed, particularly members of the high mobility group (HMG), more particularly HMG1. In combination with antisense molecules, RNAses may be used, which degrade DNA-RNA hybrids, for example, RNAseH. For integration, one may use various enzymes which aid in integration, particularly homologous recombination, e.g recombinases. Other proteins which will aid or enhance the function of the active agent may be included, as appropriate.

For preparing the liposomes, the procedure described by Kato et al., *J. Biol. Chem.* 266, 3361 (1991) may be used.

Briefly, the lipids and lumen composition are combined in an appropriate aqueous medium, conveniently a saline medium where the total solids will be in the range of about 1–10 weight percent. After intense agitation for short periods of time, from about 5–60 sec., the tube is placed in a warm water bath, from about 25°–40° C. and this cycle repeated from about 5–10 times. The composition is then sonicated for a convenient period of time, generally from about 1–10 sec. and may be further agitated by vortexing. The volume is then expanded by adding aqueous medium, generally increasing the volume by about from 1–2 fold, followed by shaking and cooling. This method allows for the incorporation into the lumen of high molecular weight molecules, particularly nucleic acids of one kbp or more, conveniently at least 5 kbp, and including 20 kbp or more. In this way plasmids, large genes, chromosomal fragments, viruses or viral segments may be introduced into cells efficiently.

To obtain the final liposomes for use, the liposomes containing the HVJ proteins and the liposomes containing the compositions to be delivered are combined in an aqueous medium, which will serve as the medium in the lumen, and incubated, as a matter of convenience, at a reduced temperature for a short period of time, generally not more than about 30 min., more usually ranging from about 5–20 min., and then combined at an elevated temperature, in the range of about 25°–40° C., for at least about 10 min., and not more than about 60 min., conveniently from about 20–45 min., with agitation. The weight ratio of the liposomes with the agent of interest to the liposomes with the fusing proteins will usually be in the range of about 1–10:1, more usually about 1–5:1. The desired liposomes may then be isolated by employing a sucrose gradient centrifugation, where the liposomes will sediment in the appropriate band.

The final liposomes will have from about 50–90 weight percent lipid, more usually from about 65–85 weight percent lipid, from about 10–50 weight percent HVJ protein, more usually from about 15–35 weight percent HVJ protein, and from about 0.1–2 weight percent of the composition to be delivered, more usually from about 0.3–1.5 weight percent and preferably from about 0.5–1.5 weight percent, frequently from about 0.5–1 weight percent.

The subject liposomes may be modified by providing molecules which will direct the liposomes to particular target tissue. These molecules may be various ligands, receptors, antibodies, or the like, which have a preference for a particular target cell. Thus, these molecules may involve ligands such as growth factors, colony stimulating factors, hormones, cytokines, immunoglobulins, where the immunoglobulin may be used because of the binding of the constant region to the particular cell or because of a specificity for a surface membrane protein, homing receptors, viral proteins, and the like. The proteins may be included in the liposome actively or passively, where the proteins may be naturally occurring or modified by having lipid groups present. Thus, depending on the nature of the molecule for targeting, the molecule may be mixed with the HVJ proteins for preparation of the HVJ liposome used as a precursor. Usually, the amount of the targeting composition will range from about 0.1–2:1 weight ratio to the HVJ proteins. Alternatively, the protein may be added to the final liposome by incubating the liposome with the protein in an appropriate medium, where the weight ratio of protein to liposomes will generally be in the range of about 0.1–10:1, more usually 0.5–2:1. Other techniques for incorporating targeting proteins are well established in literature and need not be further described here. See, for example, Sunamoto and Iwamoto, Crit. Rev. Ther. Drug Carrier Syst., 1986, 2(2)

117–136; Torchilin, ibid, 1985, 2(1) 65–115; and Guidoni et al., Tumour Biol. (Japan) 1984, 5(1) 61–73.

The liposomes may be stored or used directly for transfer to target cells. The subject liposomes may be used for delivery of the lumen compositions in vitro, in vivo, and ex vivo. Cellular targets may include solid tissue, mobile cells, particularly hematopoietic cells, normal cells, abnormal cells, e.g. neoplastic cells, psoriatic cells, neoproliferative cells, mature cells, progenitor cells, stem cells, endothelial cells, epithelial cells, stromal cells, neuronal cells, mucosal cells, cutaneous cells, vascular smooth muscle cells, hepatic cells, Kuppfer cells, etc., with the exclusion of cells of the reticular endothelial system, particularly macrophages or other cells which are naturally phagocytic. Organs which may be involved include the vasculature, heart, pancreas, mammary tissue, neuronal tissue, synovia, lymph nodes, spleen, kidneys, liver, testis, brain, thyroid, etc.

The subject liposomes may be administered in a wide variety of ways, intraluminally, intraorgan, subcutaneously, or the like. Conveniently, the subject compositions may be administered intravascularly, particularly intraarterially upstream from the target tissue. The target tissue may be subject to isolation, so as to limit the flow of blood or allow for an extended period of incubation, or the liposomes may be maintained in the region by virtue of having a specific affinity for target cells, or the liposomes may be allowed to flow through the vasculature.

The subject compositions may be used in a wide variety of situations. In vitro, the subject compositions may be used for efficient transfer of agents to cells, where the effect of the agent on the cells, either transitorily or permanently is of interest. Thus, one may introduce a large number of different compositions into the cells and determine the effect of the compositions on the cells viability, phenotype, degree of integration, or the like. For use ex vivo, one may provide opportunities for modifying organs for transplant, modifying hematopoietic cells, e.g. stem cells, vascular grafts, myoblasts, fibroblasts, keratinocytes, etc. These opportunities may include inactivation of particular cells, e.g. T-cells, labeling particular cells, so that one may monitor changes in the particular organ, introduction of novel capabilities, so that the cells may be able to produce compounds of interest, particularly for secretion, such as insulin, growth factor, cytokines, colony stimulating factors, hormones, etc. For in vivo use, not only may the purposes indicated for ex vivo be employed, but also, the subject compositions may be used in a variety of situations for prophylactic or therapeutic purposes.

The term "HVJ-liposome" refers to a vesicle which has been treated with, or associated with viral coat proteins from the Hemagglutinating Virus of Japan (HVJ) Z strain (Sendai virus; paramyxovirus) using attenuated virus, mutated virus, viral envelopes, viral spikes, viral envelope proteins, viral peptides, viral peptide fragments, recombinant viral proteins, recombinant viral fusion proteins and any combination thereof. Two glycoproteins of Sendai virus, such as HVJ, have been identified and purified. These glycoproteins consist of hemagglutinin-neuraminidase (HN) and fusion (F) proteins and they have been shown to play an important role in viral infection and membrane fusion. The HN protein has hemagglutination and neuraminidase activities and is responsible for absorption of virus to the receptor on host cells. The full-length cDNA for HN has been cloned and sequenced by Miura, et al., 1985, FEBS Letter 188:112–116. The F protein of Sendai virus consists of disulfide linked polypeptides, $F_1$ and $F_2$ which are derived by proteolytic cleavage of an inactive precursor, $F_0$. The F protein cDNA has been cloned and sequenced by Miura, et al., 1985, Gene 38:271–274. HVJ particles from mammalian cell cultures are not fusogenic or infective unless they are subjected to mild trypsin treatment to cleave the F protein to its active form. Cleavage also occurs in the chorioallantoic fluid of egg-passaged HVJ. This cleavage of $F_0$ into $F_1$ and $F_2$ is essential to the fusion activity of HVJ (Uchida, et al., 1988, Exp. Cell Res. 178:1–17). Published work reconstituting fusion liposomes using F and HN glycoproteins has indicated that a ratio of 2:1 (F:HN) results in optimal fusing activity (Nakanishi, et al., 1982, Exp. Cell Res. 141:95–101). In a most preferred embodiment of the present invention, the HVJ proteins are derived from the egg adapted Z strain of HVJ deposited with the ATCC and given accession no. ATCC VA 2388. Those skilled in the art will recognize that other proteins which perform a similar function as those from the HVJ (2) strain ATCC VR 2388, are useful in methods of the present invention; such similarly functioning elements from any virus, bacteria or cell that can mediate membrane fusion, may be substituted for the HVJ-derived elements.

The term "therapeutic agent" refers to any genetic therapeutic, protein therapeutic, or chemical therapeutic agents.

"Genetic therapeutic agent" refers to a nucleic acid agent in any form and from any natural, synthetic or recombinant source, including, but not limited to dsDNA, ssDNA, ssRNA, DNA-RNA duplex, oligonucleotides, nucleotides or nucleotide analogs, where the analogs may be included in the polynucleotide, and any combination thereof. Those skilled in the art will recognize that numerous methods exist for the preparation, isolation, synthesis, or purification of such nucleic acid agents. These agents may serve as antisense, competitive agents for binding DNA binding proteins, expression constructs for expressing a protein product, regulatory sequences, and the like.

"Protein therapeutic agent" refers to any amino acid, peptide or polypeptide agent from natural, synthetic or recombinant source, including, but not limited to, peptides, polypeptides, and fusion proteins, and wherein such agents may have the biological activity of an enzyme, a structural protein, a DNA-binding protein, a receptor protein, a hormone, a growth factor, a cell cycle dependent protein, or proteins derived or generated to act as inhibitors, as in the case of antibodies, or fragments and artificially constructed antigen binding proteins, or combinations thereof. Those skilled in the art will recognize that numerous methods exist for the preparation, synthesis, isolation, or purification of such agents for use.

"Chemical therapeutic agent", refers to any pharmacologically acceptable form of chemical compound, chemical composition, chemical drug or chemical element, or combinations thereof. Those skilled in the art will recognize that a combination of any of the above therapeutic agents may be used in single or multiple HVJ-liposomes to deliver an effective regimen of treatment to cells or screen for useful therapeutic agents according to the methods of the invention.

As disclosed herein, the genetic therapeutic agent may be in the form of a plasmid construct which contains gene constructs that can be expressed by the cells of the vasculature transfected by the methods of the invention. Construction of such expression vectors are known to those with skill in the art. In a preferred embodiment, the expression vector contains the cDNA for genes that will affect the RAS system which controls the vascular system, and is believed to play a role in hypertension and restenosis after angioplasty.

The term "non-histone nuclear protein" as used herein, refers to the protein elements found in the nucleus that are not classified as histone proteins. Those skilled in the art will recognize that these protein elements include polymerases, carrier proteins, enhancers, repressors, snRNPS, SNRPs, and are commonly known. Non-histone nuclear proteins are characterized by their behavior in isoelectric focusing gels, and can be classified accordingly. One such class is known as high mobility group-I or HMG1. Such nuclear proteins may be particularly useful to enhance and direct transport of any associated nucleic acid sequence to the nucleus. The protein to nucleic acid weight ratio will generally be in the range of 1:0.5–10, more usually 1:1–5. Any protein with similar functions would be similarly useful in the methods of the present invention.

As disclosed herein, genetic therapeutic agents may be transfected in combination with non-histone nuclear proteins via HVJ-liposomes to cells, particularly cells of the vasculature in vivo. In a preferred embodiment, this non-histone nuclear protein is of the class HMG1 (high mobility group-1). Those skilled in the art will recognize that substitution of other non-histone nuclear proteins may be made, such as those of HMG14 or HMG17, or other classes of protein to mediate the transport of the nucleotides into the nucleus.

As disclosed herein the genetic therapeutic agents may be oligonucleotides which are specific antisense oligonucleotides. Such antisense oligonucleotides are sequences complementary to mRNA of target genes and may be used for inhibition of expression of the target gene products. Antisense oligonucleotides effectively inhibit gene expression by reducing the amount of mRNA available for translation. In one embodiment of the invention, the antisense oligonucleotides which are transfected via the HVJ-liposome method are designed to inhibit genes that are involved in detrimental vascular conditions, or the formation of such conditions. Those skilled in the art would recognize that the use of one or more antisense oligonucleotides is possible by the methods of the invention. Those skilled in the art will further recognize that such agents may intervene at the level of cell division, cell differentiation, cell growth, cell activation and act on genes which include, but are not limited to, cellular growth factors, cell cycle dependent proteins, cellular kinases, cellular phosphatases, cellular receptors; including FGF, PDGF, ACE, renin, angiotensinogen, TGF-β, cdc2 kinase, cdk2 kinase, c-myb, c-myc, c-src, c-lyn, PCNA, cyclin B, and the ANGII receptor. In a preferred embodiment, the treatment of blood vessels for the prevention of restenosis after angioplasty is accomplished by the methods of the invention to transfer antisense oligonucleotides for cdc2 kinase and antisense PCNA into cells of a segment of a blood vessel in vivo via HVJ-liposomes.

The antisense containing liposomes may be used in the development of animal models. The liposomes may be administered repetitively to inhibit or enhance expression of a particular gene or family of genes and maintain the phenotype over an extended period of time, usually one or more months. Administration will usually be less frequently than every three days and may be once a week or less. It is found that the liposomes may be repeatedly administered without significant loss of effectiveness.

The antisense oligonucleotides will generally be from about 12 to 500, usually from about 15 to 50 nucleotides, where the length is governed by efficiency of inhibition, specificity, including absence of cross-reactivity, and the like.

In another embodiment, antisense oligonucleotides are transfected by the method of the invention in combination with an enzyme(s) which will degrade or delay the disassociation of antisense-mRNA complexes in the cell. In a preferred embodiment the enzyme is RNase H. Those skilled in the art will recognize that any protein or enzyme that can preferentially degrade or sequester the antisense-mRNA duplex with the intent of preventing the translation of the mRNA target, or any enzyme that will enhance the effect of the therapeutic agent may be similarly useful. In the present invention, the administration or delivery of the HVJ-liposomes involves contacting the HVJ-liposomes containing the therapeutic agent or agents with the cells of the vasculature. Those skilled in the art will recognize that the HVJ-liposomes containing one or more therapeutic agents may be provided in solution or in any other pharmacologically suitable form for administration. In a preferred embodiment, the HVJ-liposomes are suspended in BSS, or any other suitable liquid, and delivered intraluminally. Those skilled in the art will recognize that the application of the HVJ-liposome methods of this invention, may be used in combination with ex-vivo treatment of the cells of the vasculature, followed by reimplantation in vivo so as to greatly enhance the efficiency over existing methods.

Those skilled in the art will recognize that methods of the present invention can be applied to the treatment of a variety of conditions including, and not restricted to, hypertension, restenosis after angioplasty, stenosis, hyperplasia after grafting, hyperplasia after insertion of a stent, trauma associated with bypass surgery, atherosclerosis, angiogenesis, myocardial hypertrophy, vascular smooth muscle cell hypertrophy, strokes and aneurysms.

The time of incubation sufficient to deliver the therapeutic agent to the cells of the vasculature is, in a preferred embodiment of the invention, less than 30 minutes, but may be for any period of time that is both effective and practical for the in vivo isolated segment of blood vessel. The term "cells of the vasculature" as used herein, refers to the components of the vasculature tissues including, but not limited to, the endothelium and smooth muscle layer that comprises the tunica intima in larger blood vessels, the smooth muscle and connective tissue that comprise the tunica media of larger blood vessels, and the connective tissues which are termed the tunica adventitia in larger blood vessels which comprise endothelial cells, smooth muscle cells, fibroblasts, and associated extracellular matrix.

Methods of the invention may be used to screen for useful therapeutic agents to treat or prevent a medical condition or disease. This may be accomplished using the HVJ-liposome method either in vivo, in vitro, or ex vivo. The term "biological activity" is used to refer to any activity that can be assayed or measured including, but not limited to, any binding, blocking, chelating, enzymatic, agonistic, antagonistic, inhibitory, stimulatory, metabolic or structural activity.

The following Examples illustrate certain aspects of the above-described method and advantageous results. The following Examples are shown by way of illustration of certain preferred embodiments of the invention and not intended to be limiting in nature.

EXAMPLE 1

In Vitro Gene Transfer in Vascular Smooth Muscle Cells and Cultured Carotid Artery 1) SV40 T antigen cDNA expression in VSMC using HVJ-liposomes as transfer vehicles as compared with cationic liposomes As an initial step in establishing that the HVJ method could be used as an effective vehicle for in vivo gene transfer, a comparison was made between the in vitro efficiency of the HVJ-exposure method and that of an available lipofection method using cationic liposomes. For these experiments, a vascular smooth muscle cell (VSMC) system was used to examine the efficiency of gene transfer using SV40 large T antigen cDNA. The COS-7 cell line was used as a positive control, since the cells are known to be T antigen-transformed.

Cell Cultures

For these experiments, Wistar-Kyoto rat aortic smooth muscle (RASM) (passage 4–10) cells were isolated and cultured according to the method of Owens, et al., 1986, J. Cell Biol. 102:343–352. COS-7 cells were obtained from the American Type Culture Collection (ATCC). RASM cells were maintained in culture with Waymouth's medium (Gibco, Grand Island, N.Y.) supplemented with a 5% calf serum, penicillin (100 U/ml) and streptomycin (1000 µg/ml). The COS-7 cells were maintained in Dulbecco's Minimal Essential Media (DMEM) supplemented with 10% fetal calf serum, penicillin (100 U/ml) and streptomycin (1000 µg/ml). The RASM and COS-7 cells were incubated at 37° C. in a humidified atmosphere of 95% air-5% $CO_2$ with media changes every 2 days.

DNA for Transfer

Many sources of SV40 DNA encoding large T antigen are available, for example, pBR-SV40 (Kaneda, et al., 1989, Science, 243:375–378). For these experiments, a plasmid pACT-SVT was used as a source of DNA encoding SV40 large T antigen for transfection. The construction of this plasmid is described in Tomita, et al., 1992, Biochem. Biophys. Res. Comm., 186:129–134. The plasmid pACT-c-myb (from Dr. Ishii, The Institute of Physical and Chemical Research, Japan) contains the 5'-promoter region (370 base pairs) and the first intron (900 base Pairs) of the chicken β-actin gene. The KpnI/BamHI fragment of the SV40 genome containing the SV40 large T antigen gene, was cloned into pUC18. The StuI site of the construct was converted to a NcoI site using linker ligation methods. The NcoI/BamHI fragment encoding the SV40 large T antigen gene was then cloned into a similarly digested pACT-c-myb vector (excising the c-myb gene), which results in the plasmid pACT-SVT. Successful transfer of plasmid DNA to target cells would allow for the expression of the plasmid gene products. The expression of SV40 large T antigen on the surface of target cells can be detected by using commercially available labeled antibodies specific for the large T antigen.

Preparation of HVJ and HVJ-Liposomes

HVJ-liposomes were prepared with plasmid DNA and with HMG1 (High mobility group 1 non-histone nuclear protein) according to the method of Kaneda, et al, 1989, Science 243:375–378; Kato, et al., 1991, J. Biol. Chem. 266:3361–3364; and Kaneda, et al., 1989, J. Biol. Chem. 264:12126–12 129, with modification. Briefly, dried lipids of phosphatidylserine (PS), phosphatidylcholine (PC), and cholesterol were mixed in a weight/weight ratio of 1:4.8:2). This lipid mixture was combined with plasmid DNA which had been previously incubated with HMG-1 at a ratio of DNA 200 µg:HMG1 64 µg at 20° C. for 1 hour. The HMG1 was extracted from calf thymus and purified according to Goodwin, et al., 1975, Biochim. Biophys. Acta 405:280–291. This mixture, containing 10 mg lipids and 200 µg DNA, was shaken vigorously and sonicated to form liposomes by the methods described by Bangham, et al., 1965, J. Mol. Biol. 13:238–252 and Olson, et al., 1979, Biochim. Biophys. Acta 557:9–23.

HVJ Z strain (ATCC Deposit VR 2388), was propagated in the chorioallantoic fluid by the method of Okada and collaborators (see, e.g., Uchida, et al., 1979, J. Cell Biol. 80:10–20). Isolation of the egg adapted Z strain of HVJ was originally described by Okada, 1962, Experimental Cell Research 26:98–107. Briefly, the chorioallantoic fluid infected with virus was centrifuged at 3,000 RPM for 20 minutes. The supernatant was then centrifuged at 20,000 RPM for 30 minutes. The sediment is resuspended and centrifuged at 3,000 RPM for 20 minutes to eliminate aggregates.

For these experiments, stock virus, preferably 100 µl, in polypeptone solution (5 g polypeptone, 1 g NaCl, 500 ml $H_2O$, pH to 7.2 with 1N NaOH) is injected into the allantoic cavity of a 10 day old embryonated chicken egg. The inoculated egg is allowed to incubate for 3 days at 35.5° C. then cooled overnight at 4° C. The infected chorioallantoic fluid is then removed (taking care to minimize contamination with blood) and can be stored in this state at 4° C. for one month.

Further purification is performed by isolating virus in the chorioallantoic fluid by centrifugation at 2,500 RPM for 10 minutes to remove debris and isolating the supernatant. After a second centrifugation at 1,500 RPM for 5 minutes the supernatant containing the HVJ is removed; dimethylsulfoxide is added to the supernatant at a final concentration of 10% and then aliquoted (50 µl aliquots) for stock samples to be kept in liquid nitrogen.

The activity of the virus can be monitored by two procedures. A first procedure involves measuring the optical density of the virus sample at 540 nm. At this wavelength, 1 OD (Optical Density Unit) is equivalent to 15,000 HAU/ml. A second procedure requires the measurement of hemagglutinating activity directly. In this procedure, isolated chicken red blood cells (RBCs) are washed and resuspended at 5% packed cell volume to final volume in SSC. Then, 0.5 ml of HVJ is added to an equal volume of RBC solution, and a dilution curve is generated measuring hemagglutination vs. dilution.

For the preparation of HVJ-liposomes, the purified HVJ (strain Z) is inactivated by UV irradiation (110 erg/mm²/sec) for 3 minutes immediately prior to use. The liposome mixture was incubated with the inactivated HVJ and incubated for 10 minutes at 4° C. followed by an incubation of 30 minutes at 37° C.

The liposome-DNA-HMG1 mixture was incubated with the inactivated HVJ and incubated for 10 minutes at 4° C., followed by an incubation of 30 minutes at 37° C. Previous in vitro studies demonstrated an enhanced uptake of DNA using an initial drop in temperature. The HVJ-liposome complexes were collected for use in transfection, after removing free HVJ by sucrose density gradient centrifugation as described by Kato, et al., 1991, Biochem. Biophys. Res. Comm. 266:3361–3364.

Transfection Procedures and Assays

The comparison of transfection efficiency using HVJ-liposomes versus cationic liposomes as transfer vehicles was done according to the following procedures. RASM cells were inoculated on day 0 into a 4 chamber slide containing growth media. After the cells were allowed to grow to confluence, the cells were incubated with 500 µl of the HVJ-liposome complex (prepared as described above) which contained about 1.3 mg of lipids and about 5 µg of encapsulated DNA. Following a total incubation time of 35 minutes, first at 4° C. for 5 minutes and then at 37° C. for 30 minutes, the media was changed to fresh medium and the cells were cultured for 2 days. In the comparison procedure using cationic liposomes, DNA-HHG1 complex (10 μg of DNA) was mixed with Lipofectin® Reagent (GIBCO BRL Life Technologies, Gaithersburg, Md.) dissolved in an equivalent volume of dH$_2$O at a weight/weight ratio of 1:3. RASM cells grown to confluence on a 4 chamber slide were incubated with the Lipofectin®-DNA mixture for a total incubation time of 24 hours at 37° C. After incubation, the media was changed and the cells were cultured for 2 days.

After the 2 day culture, cells were fixed with 3% paraformaldehyde and screened for SV40 large T antigen expression using a murine monoclonal antibody specific for SV40 large T antigen (Oncogene Science, Manbasset, N.Y.) and an enzyme immunohistochemical staining kit (Histostain-SP kit, Zymed Labs, Inc., South San Francisco, Calif.).

Results

The results, as illustrated in FIG. 1, demonstrate that HVJ-mediated transfection is approximately 10 times more efficient than other methods, as measured by expression of SV40 large T antigen using immunohistochemical staining. When transfection by HVJ-mediated liposomes for 35 minutes incubation was compared with Lipofectin® mediated transfection for 24 hours incubation, the HVJ method was approximately 10 times more effective. Generally, lipofection methods require longer incubation times (6–24 hours) for detectable cell transfer. In a representative experiment, HVJ-liposome treatment resulted in about 20% positive staining, whereas the lipofection method only resulted in 2% staining. This indicated that the HVJ-liposome method is a highly efficient means using short incubation times for the transfer of nucleic acid sequences into normal somatic cells.

2) ACE (Angiotensin converting enzyme) cDNA expression in VSMC

In order to use the HVJ-liposome method for gene transfer in vivo, it was important to establish that transfected material would retain its biological activity. In order to test this, a plasmid containing the cDNA for an enzyme was transfected into the VSMC system to determine expression of transferred protein, and the resulting biological activity (e.g., enzyme activity) of the protein.

Transfection Procedures and Materials

A test plasmid was constructed to contain the human truncated cDNA for ACE (angiotensin converting enzyme, Lattion, et al., 1989, FEBS Letts. 252:99–104) from Rs35-15 (kindly provided by P. Corvol, INSERM, France). The ECORI fragment of RB35-15 containing the truncated ACE cDNA including two putative active sites was ligated into the pUC-CAGGS expression vector similarly digested with ECORI (provided by J. Miyazaki, Tokyo U., Tokyo, Japan). Other enzyme cDNAs and other expression vectors may be prepared and used for transfection with the HVJ-liposomes.

Determination of ACE enzyme activity per mg protein was done by measuring hippuryl-L-histidyl-L-leucine (HHL) hydrolyzing activity using the modified method of Cushman and Cheung, 1970, Biochem. Pharmacol. 20:11637–11648. For the HVJ-mediated transfer, HVJ-liposome complexes were formed as described in Section 1 above. For the lipofection-mediated transfer cationic liposomes were prepared as described in Section 1 above, and plasmid DNA (30 μg)-HMG1 was dissolved with Lipofectin® (90 μg) in 4 ml of media.

For the ACE gene transfer experiments, RASM and COS-7 cells were obtained and maintained as described in Section 1 above. COS-7 cells or RASM cultured cells (1×10$^6$ cells) were inoculated into a 60 mm petri dish and grown to confluence. HVJ-liposome complexes containing about 20 μg of encapsulated DNA were introduced to the culture and incubated at 4° C. for 5 minutes and then at 37° C. for 30 minutes, after which time the cells were washed with Balanced Salt Solution (BSS: 137 mH NaCl, 5.4 mH KCl, 10 mH Tris-HCl, pH 7.6) containing 2 mH CaCl$_2$. The DNA-Lipofectin® complexes were added to the cell culture and incubated at 37° C. for 24 hours before changing media. After incubation the cells were maintained in media supplemented with 5% calf serum for 2 days at which time ACE activity was determined as described above.

Results

Figure 2A:
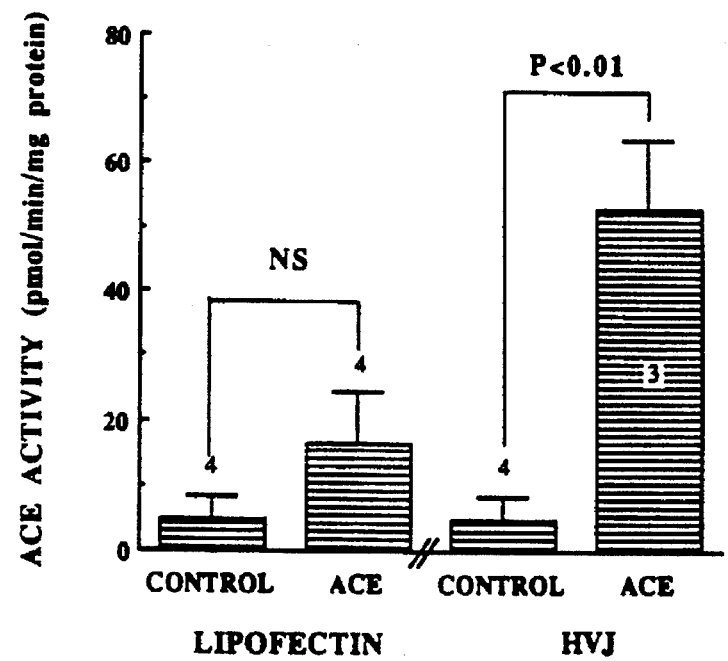
FIG. 2A and 2B are bar graphs illustrating the ACE activity of COS cells transfected via cationic liposomes (lipofectin) or HVJ-liposome transfection as described in Example 1, after 35 minutes incubation (FIG. 2A) or after 24 hours incubation (FIG. 2B).
Figure 2B:
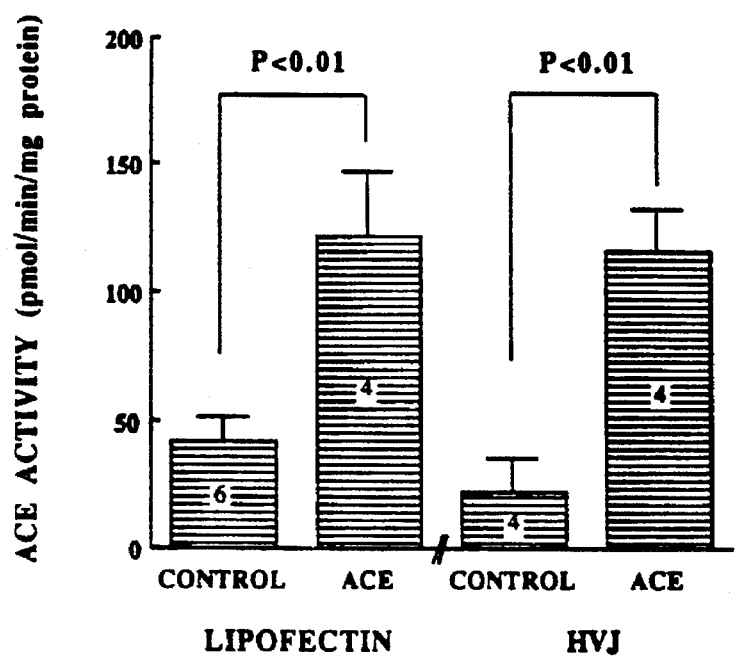

The result shown in FIG. 2 for COS cell transfection of ACE cDNA demonstrated that the ACE activity of cells transfected by the HVJ-liposome method, 35 minute incubation, showed greater ACE activity than by cationic lipofection incubated for the same amount of time. This activity, shown in FIG. 2A was 10-fold higher than the control vector-transfected cells, and approximately 3–5 times greater than by lipofection. After 24 hours incubation as shown by FIG. 2B, both methods are of approximately the same ACE activity, in contrast to the control transformation, which showed higher background for the lipofection.

After gene transfer into RASM cells, expression levels of ACE were nearly comparable when HVJ-liposomes were incubated with the cells for 35 minutes as when Lipofectin® cationic liposomes were incubated with the cells for 24 hours. However, ACE activity in cells transfected with control vector was higher (creating higher backgrounds) when Lipofectin® mediated transfer was used. These experiments demonstrated that the HVJ-liposome method is an efficient method for transfection of DNA and its expression in somatic cells using only brief (35 minutes vs. 24 hours) incubation times.

3) ACE cDNA expression in cultured rat carotid artery Artery Cultures and Assays Additional experiments were performed to demonstrate the feasibility and advantages of using the HVJ-liposome transfer method in vivo. Dissected Sprague-Dawley rat carotid arteries were cultured in situ as an experimental system. Rats weighing 400–450 g were dissected as reported by Soyombo et al., 1990, Am. J. Pathol., 137:1401–1410, after balloon catheterization (2 French Fogarty catheter, Baxter) and the carotid arteries removed and cultured in Waymouth's media without serum. The artery lumen was denuded of endothelial lining by the balloon catheter. Procedures for the denuding of the endothelium have been described, for example, by Clowes et al., 1983 lab. Invest. 49:208–215. HVJ-liposome complex (500 μl) or control vector plasmid DNA (~2.5 μg) was injected into the lumen of the artery (20 mm segments) by means of a cannula and allowed to incubate for 5 minutes at 4° C. and an additional 30 minutes at 37° C. with occlusion by ligation at both ends of the vessel. After the 35 minute incubation, the ends were opened and the vessels placed into culture with Waymouth's media supplemented with 30% fetal calf serum, penicillin (100 U/ml) and streptomycin (1000 U/ml).

After three days in such culture, the arteries were fixed in 4% paraformaldehyde, sectioned and stained using a polyclonal antiserum specific for human ACE, and the enzyme histochemical staining kit referenced in Section 1 above (Histostain-SP kit, Zymed Labs Inc., South San Francisco, Calif.).

Results

The immunohistochemical results of such experiments showed that there was positive staining in the medial layer in 3 of 4 treated vessels with over 20% of the total medial layer positively stained. None of the control vessels (neither 4 control vector transfected nor 4 untreated vessels) showed positive staining. These experiments demonstrated the effectiveness of HVJ-liposome delivery of a gene to cells in an isolated blood vessel and high-level expression of the product of the transferred gene in cells of the medial layer of the vessel.

EXAMPLE 2

In Vitro Model System for the Renin-Angiotensin System (RAS)

1) cDNA expression of ACE in VSMC:Biological Activity

The presence of the components of the RAS in VSMC has been reported by many investigators (Re, et al., 1982, Life Sci. 30:99–106; Dzau, 1984, J. Card. Pharm. 6:5377–382; Murphy, et al., 1991, Nature 351:233–236; Rakugi, et al., 1992, Clin. Res. 40:146A). AngII (angiotensin II), the final product of RAS, can induce vascular hypertrophy as well as hyperplasia both in vitro and in vivo (Itoh, et al., 1990, J. Clin. Inves. 86:1690–1697; Geiserfer, et al., 1988, Cir. Res. 62:749–756; Paguet, et al., 1990, J. Hyperten. 8:565–572; Griffin, et al., 1991, Hypert. 17:626–635). Accordingly, it has been hypothesized that vascular AngII may play an important role in vascular growth. Knowledge of the cellular mechanisms of vascular AngII production is very limited. Questions as to rate limiting steps, autocrine regulation and general regulation of the VSMC RAS system are difficult to address in vivo. Thus, the development of an in vitro VSMC RAS system using the HVJ-liposome gene transfer method would provide an excellent system for further study, as well as demonstrate the variety of applications in which the HVJ-liposome system may be used.

DNA for Transfer

The pUC-CAGGS expression vector plasmid (provided by J. Miyazaki, Tokyo U., Japan) was digested with EcoRI and an EcoRI fragment containing human truncated ACE cDNA of RB35-15 including two putative active sites (provided by P. Corval, INSERM, France) as described in Example 1 or full length rat renin cDNA (provided by K. Lynch, University of Virginia) was inserted. The pUC-CAGGS expression vector without insert was used as the control vector. CAGGS contains the entire envelope region open reading frame consisting of three translation initiation codons, which represent the N termini of the large, middle, and major surface (S) polypeptides downstream of the cytomegalovirus enhancer and the chicken beta-actin promoter.

Cell Culture

Rat aortic smooth muscle cells (RASM) (passage 4–10) were isolated, cultured and maintained as described in Example 1.

Transfection with HVJ-Liposome or Cationic Liposome Complexes

The preparation of HVJ-liposomes was described in Example 1. A DNA-HMG1 complex (200 µg:64 µg) was formed by incubation at 20° C. for 1 hour. In these experiments, the liposome suspension (0.5 ml, containing 10 mg lipids) was mixed with the inactivated HVJ (64,000 HAU) in a total volume of 2 ml BSS. The mixture was incubated at 4° C. for 10 minutes and then 30 minutes with gentle shaking at 37° C. Free HVJ was removed from the HVJ-liposomes by sucrose density gradient centrifugation as described in Example I. The top layer of the sucrose gradient containing the HVJ-liposome complex was collected for use in transfection as a tranfection vehicle.

Lipofectin® (Gibco BRL Life Technologies, Gaithersburg, Md.) was used to prepare a comparison cationic liposome transfection vehicle. Briefly, DNA (30 µg)-HMG1 complex was dissolved in 50 µl of serum free culture media (Optimem, BRL) and mixed with 50 µl of the Lipofectin®.

Reagent DOTMA (N-[1-(2,3-dioleyloxy)propyl]-N,N,N-trimethylammonium chloride) was dissolved in the same volume of $dH_2O$ as the HVJ-liposomes. The weight/weight ratio was 1:3 (DNA 30 µg, Lipofectin® 90 µg, 4 ml media). This mixture was allowed to incubate for 30 minutes at room temperature.

HVJ-liposome-mediated transfection of cultured cells was carried out as follows. Confluent cells were washed three times with BSS containing 2 mM $CaCl_2$ then 1 ml of the HVJ-liposomes (2.5 mg of lipid, 2.5–10 µg of encapsulated DNA) was added. The cells were incubated for 5 minutes at 4° C. and then for 30 minutes at 37° C. For the Lipofectin®-mediated transfection of cultured cells, 100 µl of the DNA-Lipofectin® mixture was added drop-wise to each culture dish followed by incubation for 35 minutes at 37° C.

After transfection with either HVJ-liposomes, or the Lipofectin® cationic liposomes, the medium with 5% heat-inactivated calf serum was changed to fresh medium and the cells were allowed to grow for 2 days. On the third day following transfection, cells were washed twice with PBS to remove residual media and ACE activity was measured as described in Section 2 of Example 1. Cell ACE activity was normalized by expressing activity per mg homogenate protein. Utilizing this protocol measured ACE activity was completely abolished by Quinaprilat (a specific ACE inhibitor) or neutralizing antibodies to ACE as described by Rakugi et al., 1991, Circulation (Abstr.) 84:II–113.

Synthetic Cultures and Determination of DNA/RNA Synthesis

In order to measure the rate of DNA and RNA synthesis, RASM cells were seeded and cultured in 12-well Costar culture dishes with Waymouth's medium and 5% FCS. After confluence, cells were washed three times with BSS containing 2 mH $CaCl_2$. Then, 500 µl of HVJ-liposomes (1.3 mg of lipids and 1.3–5 µg of encapsulated DNA) were added to the wells. The cells were incubated at 4° C. for 5 minutes and then at 37° C. for 30 minutes, and after changing to fresh medium with 5% calf serum, they were incubated overnight in a $CO_2$ incubator. In preparation of experiments for determination of DNA and RNA synthesis, the cells were made quiescent by placing them for 48 hours prior to the transfection in a defined serum-free medium (DSF) containing insulin ($5\times10^{-7}$M), transferrin (5 µg/ml), and ascorbate (0.2 mM), as described by Owens and Thompson, 1986, J. Cell Biol. 102:343–352. Conditioned medium (CM) was collected for 24 hours after quiescent, and was added to quiescent RASM cells in the ratio of 1:1 (vol/vol) as a bioassay for Ang II accumulation.

Relative rates of DNA and RNA synthesis were assessed by determination of tritiated thymidine and uridine incorporations into TCA (trichloroacetic acid)—precipitable material. Quiescent RASM cells grown in 12-well Costar culture dishes were pulsed for 24 hours (12–36 hours after the stimulation) with tritiated thymidine (2 µCi/ml), and 4 hours (15–19 hours after the stimulation) with tritiated uridine (2 µCi/ml), washed twice with cold PBS, twice with 10% (wt/vol) cold TCA and incubated with 10% TCA at 4° C. for 30 minutes. Cells were rinsed in ethanol (95%) and dissolved in 0.25N NaOH at 4° C. for 3 hours, neutralized and the radioactivity determined by liquid scintillation spectrometry as described by Itoh, et al., 1990, J. Clin. Invest. 86:1690–1697.

Results

Results showed that RASM cells transfected with ACE cDNA using HVJ-liposomes showed a 2-fold higher ACE activity than control vector-transfected RASM cells. In contrast, RASM cells transfected with ACE cDNA using Lipofectin® cationic liposomes did not show ACE activity greater than control transfected cells. Total protein content of the RASM cells was not affected by either transfection method.

Figure 3A:
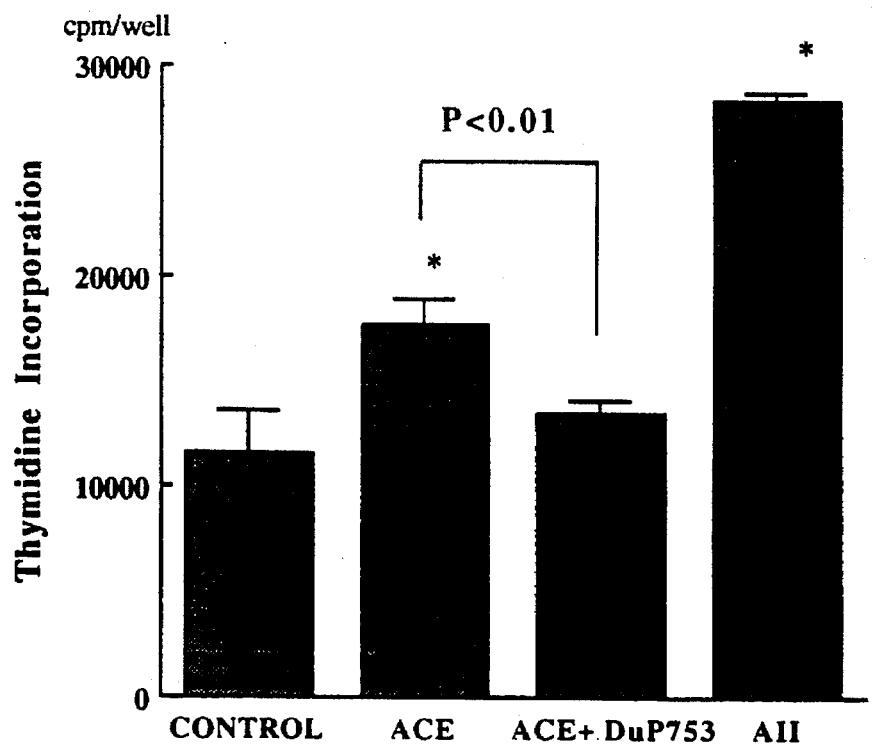
FIG. 3A and 3B are bar graphs illustrating the activity of ACE as measured by thymidine (FIG. 3A) or uridine (FIG. 3B) incorporation in vascular smooth muscle cells (VSMC) transfected as described in Example 2. ACE is angiotensin converting enzyme cDNA; AII is angiotensin II; DuP753 is an Ang II receptor antagonist (Dupont-Merck Co.).
Figure 3B:
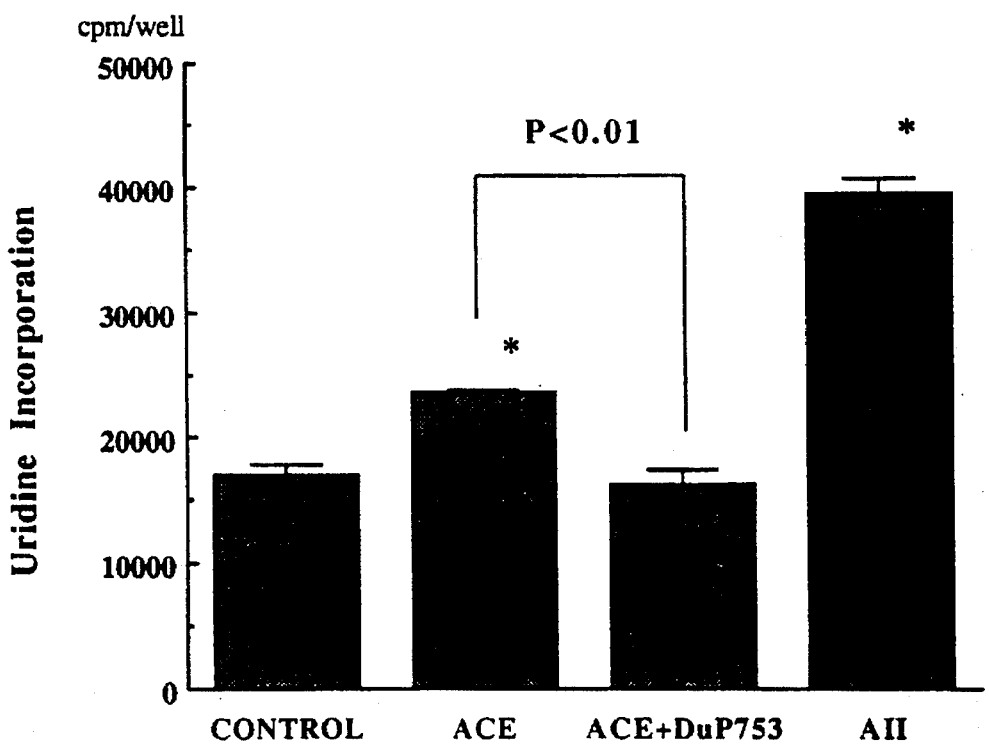

The transfection of the ACE cDNA was operable as illustrated by experiments to stimulate ACE transcription and translation. These results were confirmed by assay for DNA synthesis by measuring thymidine incorporation, and by assay for RNA synthesis by measuring uridine incorporation after induction by the addition of ANGII. These results show, in FIG. 3, that DNA and RNA synthesis in ACE-transfected RASM cells increased significantly when compared to controls (control-vector transfected and untreated RASM cells). The increase in DNA synthesis upon addition of ANGII, as shown in FIG. 3A, is effectively blocked by the addition of a specific ANGII receptor antagonist (Al IRA or DuP753). The increase in RNA synthesis, as shown in FIG. 3B was also blocked by the addition of specific Ang II receptor antagonist (DuP753 at $10^{-6}$M, Dupont-Merck Co.). Addition of exogenous Ang I (Sigma Chemical Co., St. Louis, Mo.) stimulated RNA synthesis in a dose dependent manner in both control and transfected RASM cells. There was a consistently higher uridine incorporation rate in ACE-transfected cells than in control cells at any concentration of Ang I. The Ang I ($10^{-7}$M) induced increase in RNA synthesis in the ACE-transfected RASM cells could be inhibited by the addition of DuP753 ($10^{-6}$M, Ang II receptor antagonist). Transfection with higher amounts of ACE cDNA stimulated RNA synthesis in a dose dependent manner (20 μg–400 μg).

Treatment of quiescent cells with CM from ACE-transfected cells resulted in significant increase in RNA synthesis activity as compared with GM from control cells.

2) ACE and RENIN cDNA expression in VSMC

Transfection Procedures and Materials

In other experiments, renin cDNA (full length rat renin cDNA from Kevin Lynch, U. of Va.) or both renin and ACE cDNAs were used to transfect RASM cells as described above, using HVJ-liposomes. Transfection of renin cDNA stimulated RNA synthesis in the RASM cells. The co-transfection of renin cDNA and ACE cDNA resulted in a 2-fold increase in RNA synthesis over that of cells transfected with ACE cDNA alone. This was a 4-fold increase over control cells and over transfection via Lipofectin®. The RNA synthesis activity of co-transfectants was also inhibitable by the addition of the Ang II receptor antagonist Dup753.

Incubation with conditioned media (CM) collected from ACE-transfected RASM cells also resulted in significant increase in RNA synthesis of quiescent RASM cells (as bioassay) as compared to incubation with CM from control vector-transfected RASM cells. This increase in RNA synthesis was significantly reduced by DuP753 ($10^{-6}$M).

Results

These results demonstrated the usefulness of the HVJ-liposome method for transfecting somatic cells after only a short incubation time (35 minutes) using genes of the RAS system. The biological activity of the RAS system gene products after such transfection using HVJ-liposome remained intact. These results are in contrast to previous results with cationic liposomes, due to problems with toxicity and cell death using such liposomes. Thus, the HVJ-liposome method can efficiently operate using short incubation times with efficiency that yields expression and biological activity where lipofection fails. The use of this HVJ-liposome method and the cotransfection of different DNAs permit the manipulation of specific target tissues.

EXAMPLE 3

In Vitro Use of Antisense Oligonucleotides in VSMC By HVJ-transfer

1) The effect of Antisense (AS)—basic Fibroblast Growth Factor (bFGF) via HVJ-liposome transfer as compared with lipofection and direct oligonucleotide transfer The antisense approach is an innovative strategy to block the transcription or translation of specific genes. However, the efficacy of antisense oligonucleotides for in vitro and in vivo studies has been limited by low efficiencies of uptake (Marcus-Sekura, 1988, Analytical Biochem. 172:289–295) and by instability due to degradation by nucleases (Wickstrom, 1986, J. Biochem. Biophys. Methods 13:97–102). These problems have restricted the effectiveness of antisense oligonucleotides both in vitro and in vivo. Modifying the backbone of the oligonucleotides such as phosphorothioate increases the resistance to nuclease (Agrawal, et al., 1991, Proc. Natl. Acad. Sci. 88:7595–7599; Loke, et al., 1988, Curr. Topics Micro. Immunol. 141:282–289). However, significant degradation still occurs via the lysosomal pathway after uptake. Furthermore, a high concentration is needed because uptake into cells is still low and the efflux from endosomal components is also needed (Agrawal, et al., 1991, Proc. Natl. Acad. Sci. 88:7595–7599; Loke, et al., 1988, Curr. Topics Micro. Immunol. 141:282–289). In these experiments, the HVJ-liposome method as described in Examples 1 and 2 was used to effect the delivery of antisense oligonucleotides against a growth factor into cells in vitro as compared with lipofection-mediated or direct oligonucleotide transfer. Specifically, the effect of oligonucleotides against AS-FGF on RASM cells was compared using HVJ-liposomes, Lipofectin-liposome or direct oligonucleotide transfer. RASM (passage 4–10) were isolated and cultured from 3 month old Wistar-Kyoto rats and then maintained in culture as described in Example 1.

Preparation of Oligonucleotides

A variety of oligonucleotide sequences against a number of growth factors of interest (including TGF-$\beta_1$, bFGF and PDGF A chain) may be synthesized and purified. The anti sense (AS) oligonucleotides prepared for the experiments described herein correspond to sequences of the human basic fibroblast growth factor (bFGF) gene reported by Morrison, 1991, J. Biol. Chem. 266:728–734 ([SEQ ID NO:1] antisense: 5' GGC-TGC-CAT-GGT-CCC-3'; [SEQ ID NO:2] sense: 5 '-GGG-ACC-ATG-GCA-GCC3'). This antisense oligonucleotide inhibits FGF synthesis specifically in RASM cells. Unmodified 15-base deoxyribonucleotides are synthesized on an automated solid-phase synthesizer (Applied Biosystems Incorporated) using standard phosphoramide chemistry. The synthesized oligonucleotides are washed with 70% ethanol, dried, then resuspended in sterile TE buffer (10 mM Tris, 1 mM EDTA). The solution containing the oligomers is then purified by gel filtration over a NAP10 column (Pharmacia) and quantitated by spectrophotometer. Prior to use, the purified oligomers were ethanol-precipitated, lyophilized to dryness, and dissolved in the culture media.

Preparation of HVJ-Liposomes, Transfection Procedures and Cell Growth Assays

HVJ-liposomes were prepared as described in Example 1. Phosphatidylserine, phosphatidylcholone, and cholesterol were mixed in a weight ratio of 1:4.8:2 (Kato, et al., 1991, J. Biol. Chem. 266:3361–3364; Kaneda, et al., 1989, J. Biol. Chem. 264:12126–12129). The lipid mixture (10 mg) was deposited on the sides of a flask by removal of tetrahydrofuran in a rotary evaporator. HMG1 was purified from calf thymus as described in Example 1. Dried lipid was hydrated in 200 µl of balanced salt solution (BSS; 137 mM NaCl, 5.4 mM KCl, 10 mM Tris-HCl, pH 7.6) containing sense or antisense oligonucleotides (10 nmoles). The control was BSS (200 Hl) alone. The liposome-oligonucleotide complex suspension was prepared by vortex, sonication for 3 seconds, and shaking for 30 minutes. Purified HVJ (strain Z) was prepared and inactivated by UV irradiation as described in Example 1. The liposome suspension (0.5 ml, containing 10 mg lipids) was mixed with 20,000 HAU inactivated HVJ in a total volume of 4 ml BSS. The mixture was incubated at 4° C. for 5 minutes and then 30 minutes with gentle shaking at 37° C. Free HVJ was removed from the HVJ-liposomes by sucrose density gradient centrifugation and the top layer containing the HVJ-liposome complex was collected for use as described in Example 1. The final concentration was equivalent to about 0.25 µM calculated, as described by Kato, et al., 1991, J. Biol. Chem. 266:3361–3364 and Kaneda, et al., 1989, J. Biol. Chem. 264:12126–29.

Lipofectin® (Gibco BRL Life Technologies, Gaithersburg, Md.) was used to prepare a comparison cationic liposome transfection vehicle. Oligonucleotides (2.5, 5.0 or 20 µM) were dissolved in 50 µl of serum free culture media (Optimem, BRL) and mixed with 50 µl of the Lipofectin® Reagent DOTMA (N-[1-(2,3-dioleyloxy)propyl]-N,N,N-trimethylammonium chloride) dissolved in the same volume of $dH_2O$ in a weight/weight ratio of 1:6 (DNA:Lipofectin). This was found to be less toxic than when the weight/weight ratio was 1:3. This mixture was allowed to incubate for 30 minutes at room temperature.

After RASM cells were allowed to reach confluence, they were washed three times with BSS containing 2 mM $CaCl_2$ and treated either with 500 µl of HVJ-liposomes (1.3 mg lipid, 0.25 µM encapsulated oligonucleotides) or oligonucleotide solution (10 µl in BSS added to the wells) or with 100 µl of cationic liposomes. The cells treated with the HVJ-liposomes were incubated at 4° C. for 5 minutes then for 30 minutes at 37° C. The cells treated with oligonucleotides alone or with cationic liposomes were incubated at 37° C. for 35 minutes. The media was then replaced with fresh media without calf serum, and the cells were allowed to incubate overnight at 37° C. in a $CO_2$ incubator.

Determination of rate of DNA synthesis was done by measuring tritiated thymidine incorporation into TCA-precipitable material. Quiescent RASM cells grown in 24-well Costar culture dishes according to Owens and Thompson, 1986, J. Cell Biol. 102:343–352 as described in Example 2, pulsed for 8 hours at the studied time period (either at 20–28 hours or at 68–76 hours after stimulation) with tritiated thymidine (2 KCi/ml), then washed twice with cold PBS, washed twice with 10% (w/v) cold TCA and incubated in 10% TCA at 4° C. for 30 minutes. Cells were then rinsed in ethanol (95%) and dissolved in 0.25N NaOH at 4° C. for 3 hours, neutralized, and counted by liquid scintillation spectrometry as described by Itoh, et al., 1992, Biochem. Biophys. Res. Comm. 188:1205–1213.

Measurement of mitochondrial dehydrogenase activity (MDA) was done to determine the cell growth using a commercial kit. In preparation of experiments for determination of MDA, the cells were grown in 24 well Costar culture dishes to be confluent. After confluence, cells were washed three times with BSS containing 2 mM $CaCl_2$. Then, 500 µl of HVJ-liposomes (1.3 mg of lipids and 0.25 µl of encapsulated oligonucleotides) or oligonucleotides solution (10 µl in BSS) was added to the wells. The cells were incubated at 4° C. for 5 minutes and then at 37° C. for 30 minutes, and after changing to fresh DSF with Ang II ($10^{-6}$M; Sigma Chemical Co., St. Louis, Mo.) or vehicle, they were incubated in a $CO_2$ incubator overnight. At day 1, the medium was again changed to DSF with Ang II or none, and at day 4 the cells were used for the MDA assay. MDA was measured by cell growth determination kit (Sigma Chemical Co., St. Louis, Mo).

FGF is known to be a strong growth stimulant in VSMC. Ang II has been shown to stimulate FGF and TGF-beta mRNA and RASM cells.

Statistical Analysis

All values were calculated expressed as mean ±SEM. All experiments were repeated at least three times. Analysis of variance with subsequent Duncan's test was used to determine significant differences in multiple comparisons. $P<0.05$ was considered significant.

Results

Figure 4A:
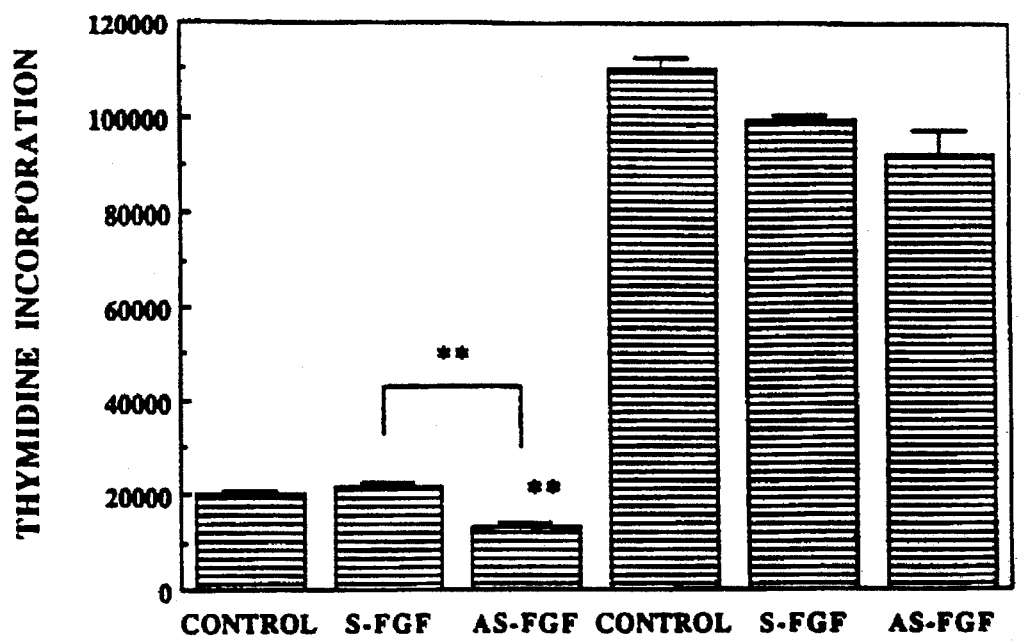
FIG. 4A and 4B are bar graphs illustrating the effect of transfection of antisense FGF oligonucleotides via cationic liposomes into VSMC under basal or Ang II stimulated conditions, as measured by thymidine incorporation, described in Example 3, 20–28 hours after transfection (FIG. 4A) and 68–76 hours after transfection (FIG. 4B). Ang II is angiotensin II added at $10^{-6}$M.
Figure 4B:
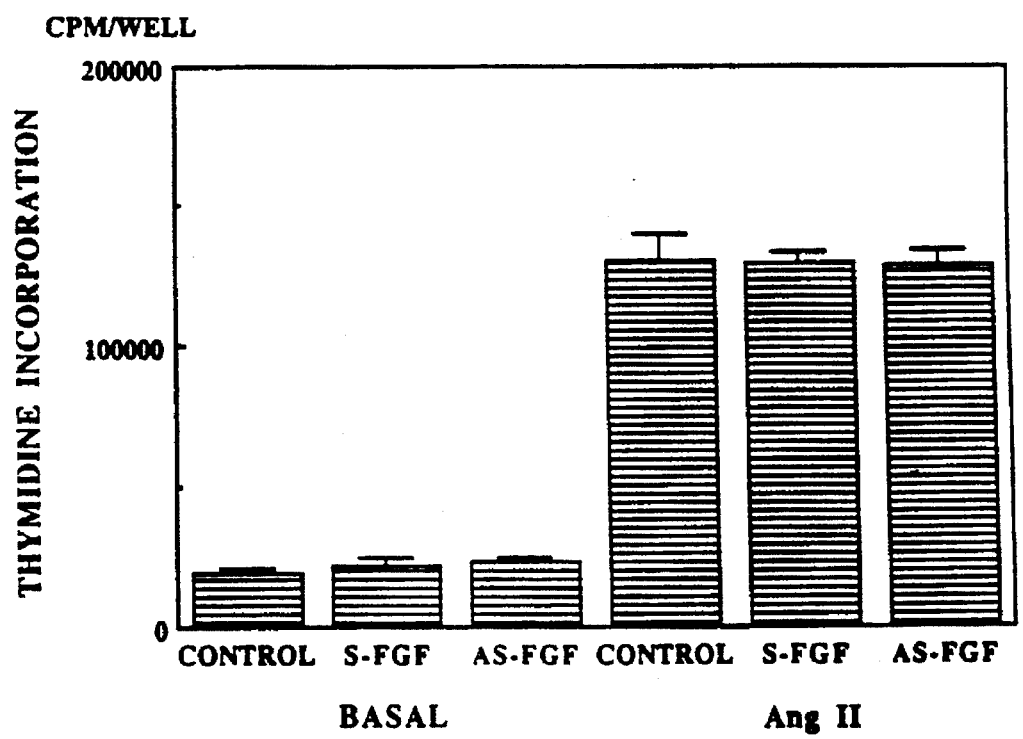
Figure 5A:
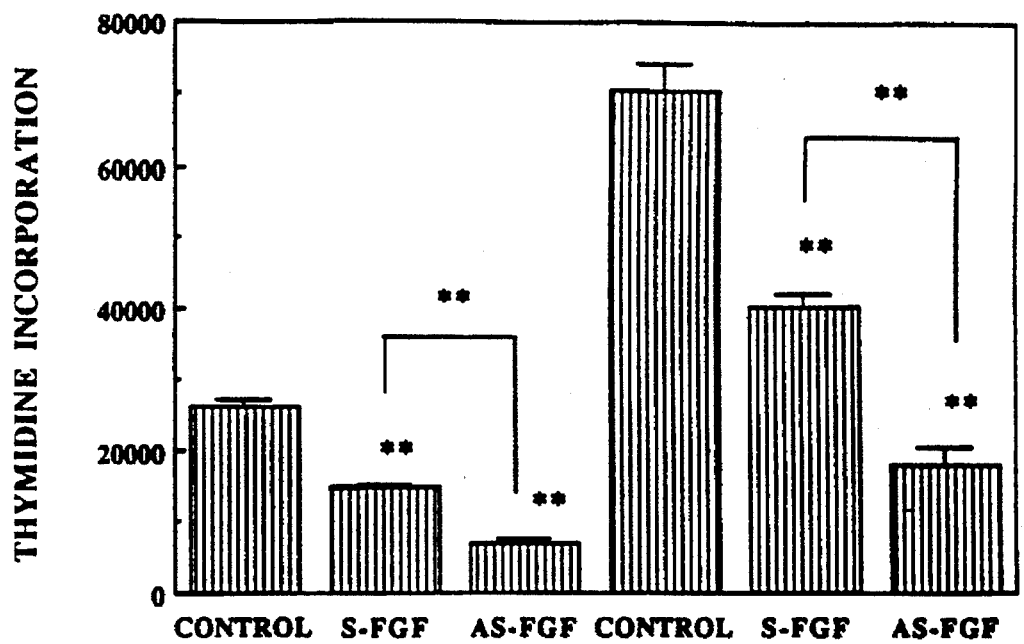
FIG. 5A and 5B are bar graphs illustrating the effect of transfection of antisense or sense FGF oligonucleotides as compared with a control via HVJ-liposomes into VSMC, as measured by thymidine incorporation, as described in Example 3, 20–28 hours after transfection (FIG. 5A) and 68–76 hours after transfection (FIG. 5B). Ang II is angiotensin II added at $10^{-6}$M.
Figure 5B:
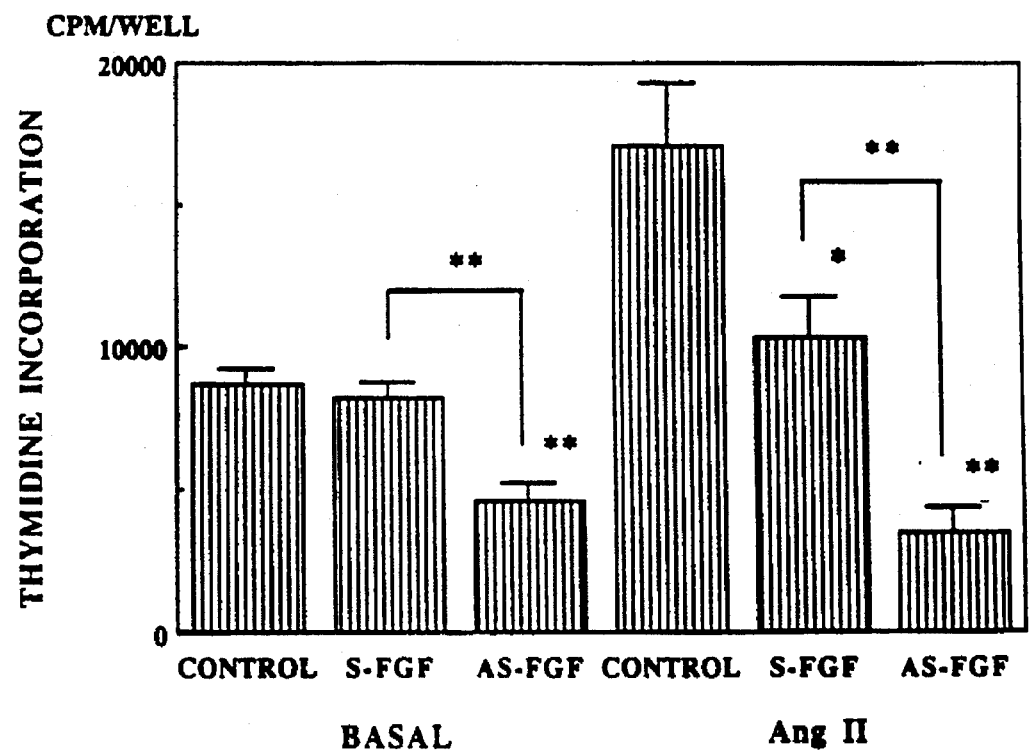
Figure 6:
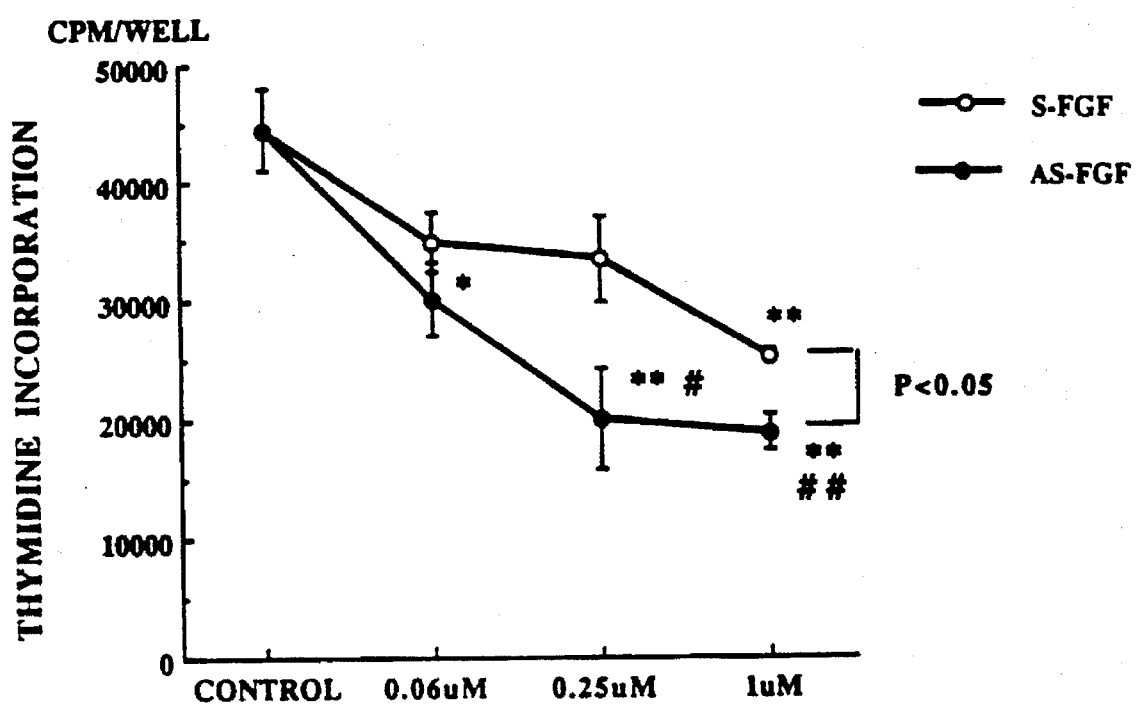
FIG. 6 is a graph illustrating the effect of HVJ-mediated transfection of antisense FGF oligonucleotides (closed circles) as compared with sense FGF oligonucleotides (open circles) at concentrations of 0.06 µM, 0.25 µM and 1.0 µM.
Figure 7A:
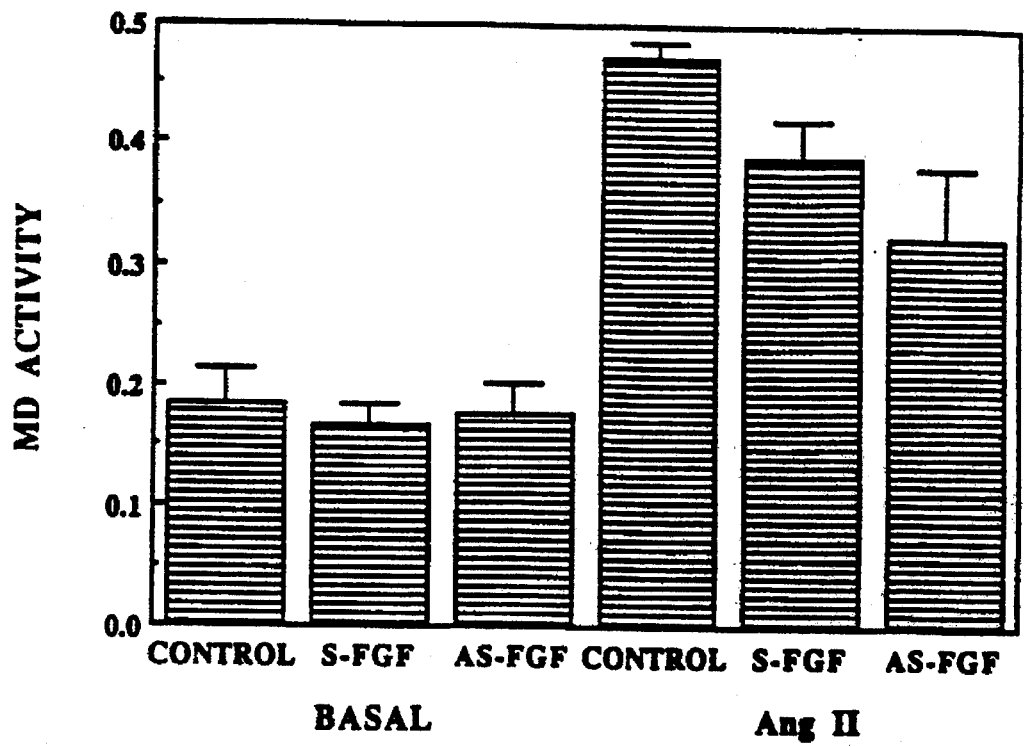
FIG. 7A and 7B are bar graphs illustrating the effect of antisense FGF on VSMC mitochondrial dehydrogenase activity (MDA) under basal or Ang II stimulated conditions, measured as described in Example 3, for non-HVJ (lipofectin) liposomal transfection (FIG. 7A) and HVJ-liposome mediated transfection (FIG. 7B). Ang II is angiotensin II administered at $10^{-6}$M.
Figure 7B:
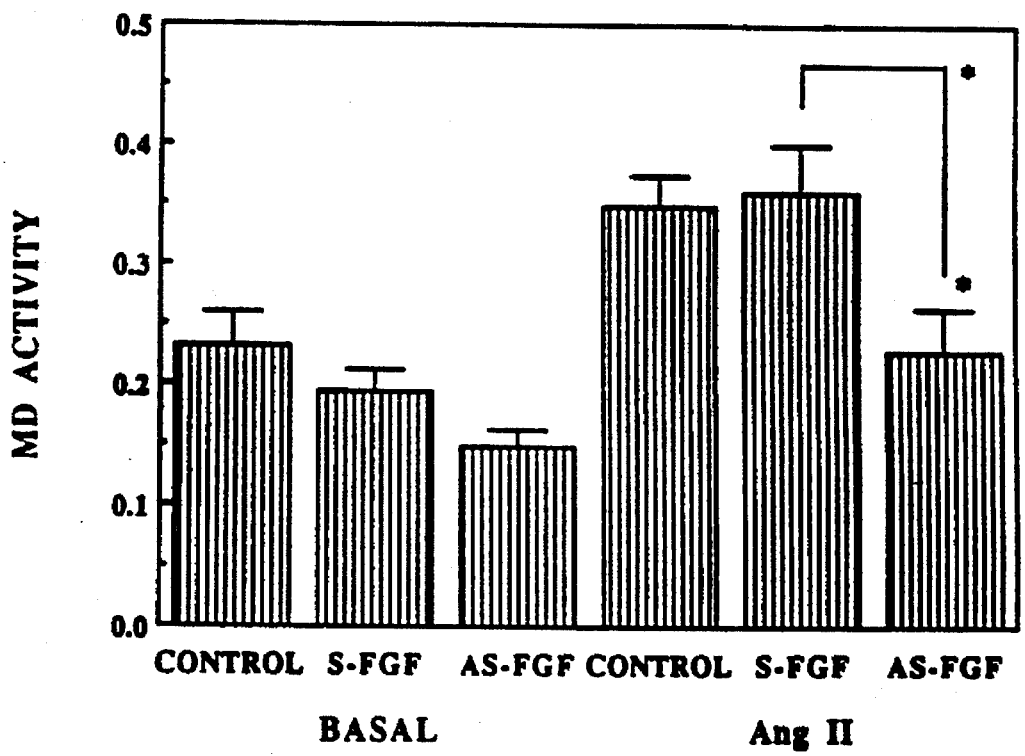
Figure 8:
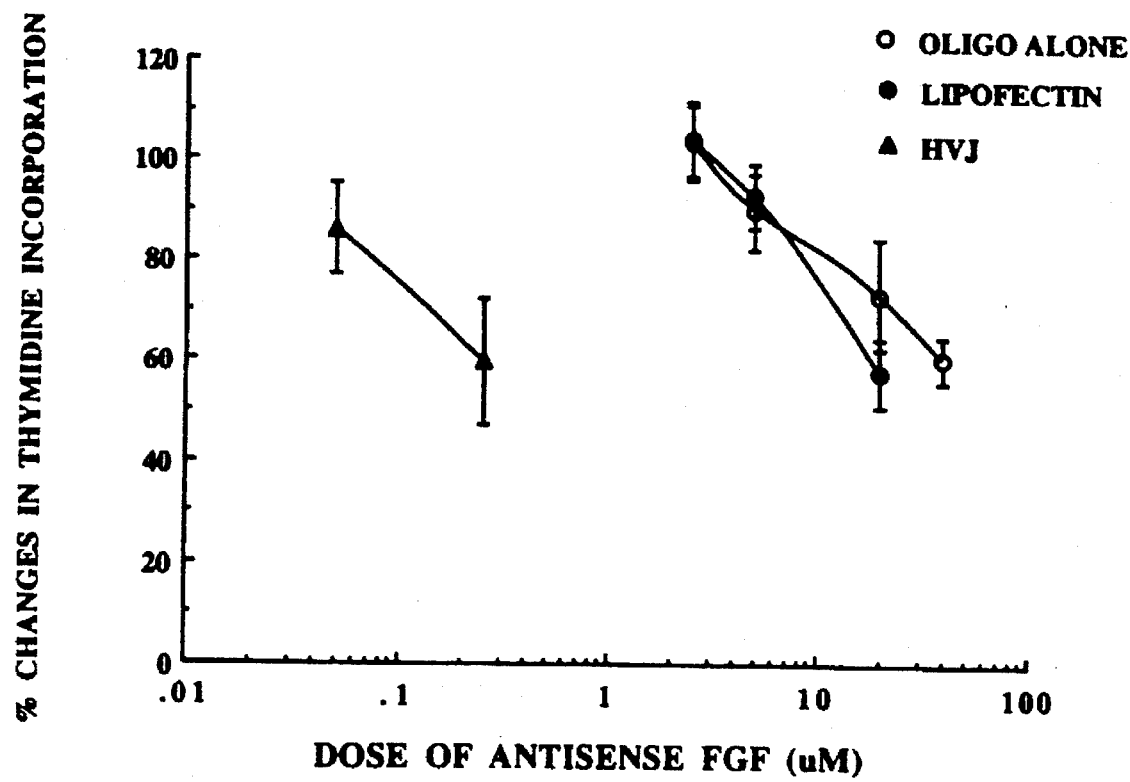
FIG. 8 is a graph comparing the efficiency of transfection as measured by the percent changes in thymidine incorporation versus dose of oligonucleotide for VSMC after transfection of antisense FGF by HVJ-liposomes (closed triangle), cationic liposomes (closed circle), or oligonucleotides alone (open circle).

FIG. 4 shows the effect of AS-FGF [SEQ ID NO:1] on DNA synthesis with oligonucleotides alone during 20–28 hours (4A) and 68–76 hours (4B) after transfection. AS-FGF [SEQ ID NO:1] inhibited DNA synthesis under basal conditions, while AS-FGF [SEQ ID NO:1] did not affect DNA synthesis of RASM cells under Ang II stimulation. During 68–76 hours after transfection, there was no significant change among three groups with oligonucleotides alone. On the other hand, with HVJ-liposome method, AS-FGF [SEQ ID NO:1] inhibited basal Ang II stimulated DNA synthesis with the HVJ-liposome method both during 20–28 and 68–76 hours after transfection, as shown in FIG. 5A and 5B, respectively. There was no significant difference between untreated and control transfected RASM cells (untreated RASM cells: 9940±566 cpm/well VS. control transfected RASM cells: 10017±1028 cpm/well). The AS-bFGF [SEQ ID NO:1] when administered using the HVJ-liposome method inhibited basal DNA synthesis in a dose dependent fashion as shown by FIG. 6. When sense bFGF (S-bFGF) [SEQ ID NO:2] as a control was administered via the HVJ-liposome method, there was a decrease in thymidine incorporation levels as compared with control groups, although this decrease could have been due to the non-specific effect of free cold thymidine. Therefore, in order to clarify the specificity of the inhibition of DNA synthesis by AS-bFGF [SEQ ID NO:1] treatment, the activity of living cells was measured via mitochondrial dehydrogenase activity (MDA), which reflects cell number (Mossman, 1986, J. Immunol. Methods 65:55) instead of by $^3$H-thymidine incorporation. AS-bFGF [SEQ ID NO:1] transfected by the HVJ-liposome method significantly lowered MDA in Ang II stimulated RASM cells as seen in FIG. 7B. In contrast, using non-HVJ liposome methods, MDA activity in the AS-bFGF [SEQ ID NO:1] treated group was not affected under basal or Ang II stimulated conditions, FIG. 7A. In FIG. 8, the effectiveness of HVJ-liposome transfer is illustrated as compared with lipofection, and transfer of the antisense oligonucleotide alone. The $ED_{25}$ of inhibitory effect on thymidine incorporation was compared, as shown in FIG. 8, using the HVJ-liposomes (closed triangles), cationic liposomes (closed circles) and oligonucleotides alone (open circles). The $ED_{25}$ inhibitory effect on vascular growth using the HVJ method is about 0.1 μM antisense oligonucleotide in the HVJ-liposome, but the other methods require a much greater concentration of oligonucleotides to obtain the same inhibitory effect to HVJ method. The $ED_{25}$ using the cationic liposomes was 10 μM; the $ED_{25}$ using oligonucleotides alone was 20 μM.

In summary, the results of these experiments showed that transfection with AS-FGF [SEQ ID NO:1] by HVJ-liposome method inhibited DNA synthesis and MDA activity of RASM cells over 68 hours, while non-HVj methods using much higher concentration of AS-FGF [SEQ ID NO:1] showed a short lived effect (20–28 hours) which was not detectable at 60 hours. This finding is also supported by FIG. 4. $ED_{25}$ of the inhibitory effect of AS-FGF [SEQ ID NO:1] using the HVJ-liposome method is much lower when compared with the $ED_{25}$ using either the cationic liposome method and using oligonucleotides alone. The high efficiency of HVJ method shown in this study may be due to the unique mechanism of HVJ method. While not wishing to be bound by theory or mechanism, the HVJ method may utilize the cellular fusion system, and therefore bypass endocytosis-mediated entry into cells. The mechanism of cellular uptake of oligomers is not well understood. The uptake of unmodified oligomers has been reported to be via the receptor mediated endocytosis, with most oligomers localized in endosomes. These experiments demonstrated the prolonged and enhanced effect of AS oligomers with HVJ-liposome method. This effect may be due to the difference of cellular uptake mechanisms. Furthermore, this prolonged effect of AS-FGF [SEQ ID NO:1] was demonstrated in MDA assays indicating that AS-FGF [SEQ ID NO:1] inhibited RASM cells growth under Ang II stimulation by HVJ-liposome method.

EXAMPLE 4

In vivo Gene Therapy by HVJ-mediated Transfer into Intact Blood Vessels

1) Expression of SV40T antigen in adult rat blood vessels
DNA for Transfer

Many sources of SV40 DNA encoding large T antigen are available. For these experiments, the expression plasmid pACT-SVT was used as a source of DNA encoding SV40 large T antigen. The construction of this plasmid is described in Tomita, et al., 1992, Biochem. Biophys. Res. Comm., 186:129–134. The plasmid pACT-c-myb (from Dr. Ishii, The Institute of Physical and Chemical Research, Japan) contains the 5'-promoter region (~370 bp) and the first intron (~900 bp) of the chicken β-actin gene. The KpnI/BamHI fragment of the SV40 genome containing the SV40 large T antigen gene, was cloned into pUC18. The StuI site of the construct was converted to a NcoI site using linker ligation methods. The NcoI/BamHI fragment encoding the SV40 large T antigen gene was then cloned into a similarly digested pACT-c-myb vector (excising the c-myb gene), which results in the plasmid pACT-SVT. For these experiments, a control vector, pACT-CCv, which does not contain the large T antigen gene, is used.

Cell Cultures

For these experiments, RASM cells (passage 4–10) were isolated, cultured and maintained as described in Example 1.

Preparation of HVJ-liposomes

The preparation of HVJ-liposomes was as described in Example 1. Briefly, PS, PC and cholesterol were mixed in a weight ratio of 1:4.8:2. The lipid mixture (10 mg) was deposited on the sides of a flask by removal of tetrahydrofuran in a rotary evaporator. HMG1 was purified from calf thymus as described in Example 1. DNA-HMG1 complexes (200 μg:64 μg) were formed by incubation at 20° C. for 1 hour. Dried lipid was hydrated in 200 μl of balanced salt solution (BSS; 137 mM NaCl, 5.4 mM KCl, 10 mM Tris-HCl, pH 7.6) containing the DNA-HMG1 complex that had previously been incubated at 20° C. for 1 hour. Liposome-DNA-HMG1 complex suspension was prepared by vortex, sonication for 3 seconds, and shaking for 30 minutes. Purified HVJ (strain Z) was prepared and inactivated by UV irradiation (110 erg/mm$^2$/sec) for 3 minutes just prior to use as described in Example 1. The liposome suspension (0.5 ml, containing 10 mg lipids) was mixed with HVJ (35,000 HAU) in a total volume of 2 ml BSS. The mixture was incubated at 4° C. for 10 minutes and then 30 minutes with gentle shaking at 37° C. The incubation at 4° C. may be omitted and the incubation initiated at 37° C. Free HVJ was removed from the HVJ-liposomes by sucrose density gradient centrifugation. The top layer of the sucrose gradient containing the HVJ-liposome complex was collected for use as described in Example 1.

Procedures for In Vivo Gene Transfer

The in vivo gene transfer experiments were performed using the left carotid arteries that had been surgically exposed in anesthetized male Sprague-Dawley rats (400–500 g). Ketamine hydrochloride (80 mg/kg) (Parke-Davis, Morris Plains, N.J.) may be used for anesthesia. A 2 French-Fogarty catheter (Baxter, Calif.) was used to induce endothelial injury in the vessels. Three treatment procedures were compared in these experiments: (1) HVJ-liposome-DNA complexes including SV40 T antigen DNA (300 μg DNA; 94 μg HMG1) or control vector plasmid DNA are directly infused into denuded carotid arteries after temporary isolation of the distal half of the artery with ligatures; (2) HVJ-liposome-DNA complexes including SV40 T antigen or control vector plasmid DNA are infused into isolated non-denuded carotid arteries by means of a cannula in the external carotid, and allowed to incubate for 30 minutes at room temperature, after the isolated segment is washed briefly with heparin-PBS to remove blood; and (3) HVJ-liposome-DNA complexes including SV40 T antigen or control vector plasmid DNA are infused by means of a cannula in the external carotid after carotid arteries are denuded by passage and inflation of a balloon catheter through an arteriotomy in the external carotid artery, where the distal half of the artery is temporarily isolated with ligatives, and allowed to incubate for 30 minutes at room temperature, and after the isolated denuded segment is washed with heparin-PBS to remove blood and debris. The external carotid segment was ligated after removal of the catheter, blood flow was restored, and the wound was closed. One week after treatment, the animals were sacrificed and the carotid arteries removed after perfusion fixation with 4% paraformaldehyde. The fixed artery segments were sectioned and tested for SV40 large T antigen expression by immunohistochemical staining as described in Example 1.

Transfected DNA was detected by polymerase chain reaction (PCR). Extraction of the DNA for PCR amplification was carried out on carotid arteries which were rinsed with PBS and flash frozen in liquid nitrogen and stored at −80° C. until DNA extraction. DNA was extracted from each segment of transfected arteries by a DNA extraction kit (Stratagene, Calif.). Extracted DNA was quantified by measuring absorbance at 260 nm. PCR amplification of 0.5 Kg aliquots of extracted DNA were performed with oligonucleotide primers complementary to the SV40 large T antigen gene (5' primer [SEQ ID NO:3]: 5'-TAGAACTCTTGCTTGCTTTGCTA-3'; 3' primer [SEQ ID NO:4]: 5'-CATTGCATACTCTGTTACAAGCT-3'). These primers have been used to amplify a sequence of approximately 300 base pairs. Thirty cycles of PCR amplification were used.

As a control both for the integrity of the extracted genomic DNA and for the PCR protocol, an aliquot of each DNA sample was also amplified with oligonucleotide primers complementary to the rat beta-actin gene (5' primer [SEQ ID NO:5]:5'-TTGTAACCAACTGGGACGATATGG-3'; 3' primer [SEQ ID NO:6]:5'-GATCTTGATCTTCATGGTGCTAGG-3', Clontech Laboratories Inc., Calif.). These primers have been used to amplify a sequence of approximately 764 base pairs. To avoid contamination of tissue samples with trace amounts of experimental DNA, extreme care was taken. Aliquots of DNA from both experimental and negative control aortas were amplified simultaneously, with the same reagents, by individuals blinded to the identity of the samples. Amplification products were electrophoresed through 2% agarose gels stained with ethidium bromide. As a positive control and semi-quantitative determination of the number of transfected cells, aliquots of DNA from $10^3$–$10^6$ cultured COS-7 (T antigen positive) cells were used. These positive controls were amplified simultaneously with samples. At least three aliquots of each DNA extract were subjected to separate PCR amplifications in all experiments.

Results

Detection of Transferred SV40 Gene by PCR

To evaluate the in vivo gene transfer by HVJ method, PCR analysis was performed in the SV40 T antigen gene transfected uninjured vessels. PCR analysis detected the T antigen gene in 7 of 9 T antigen gene transfected uninjured vessels, while it did not detect a band in any of 9 control-vector transfected vessels. This band (about 300 bp) was easily visualized by ethidium bromide staining of the agarose gels. Semiquantitative analysis of T antigen gene was performed using COS 7 cells that express T antigen as standard. DNA from T antigen gene transfected arteries was approximately equal to or more than that from $10^3$ to $10^4$ COS 7 cells. A previous report using a different method reported fewer than 100 transduced cells (Fugelman, et al., 1992, Low level in vivo gene transfer into the arterial wall through a perforated balloon catheter. Circulation 85:1110–1117). In all experiments, aliquots of DNA were amplified by PCR with rat beta-actin primers [SEQ ID NO:5 and 6], with the same PCR protocol as used for the detection of T antigen gene, yielding a band (735 bp), easily visible with ethidium bromide stained-agarose gels. The intensity of the ethidium-stained band by actin-PCR amplifications was virtually identical in all of the tissue samples. Thus, the results of PCR analysis one week after transfection revealed persistent DNA in parallel with the immunostaining results.

In Vivo Gene Transfer

Results from using treatment protocol 1, that is, the direct infusion of the HVJ-liposome-DNA complexes with no incubation, were negative as assayed for by staining with antibodies to SV40 large T antigen and PCR of T antigen sequences. Incubation of the vessel with HVJ-liposomes for 30 minutes yielded positive expression of T antigen in the isolated vessel segment (e.g., treatment protocol 2). HVJ-mediated transfection occurred in both denuded (e.g., treatment protocol 3) and intact blood vessels (e.g., treatment protocol 2) to approximately equal levels.

Figure 9A:
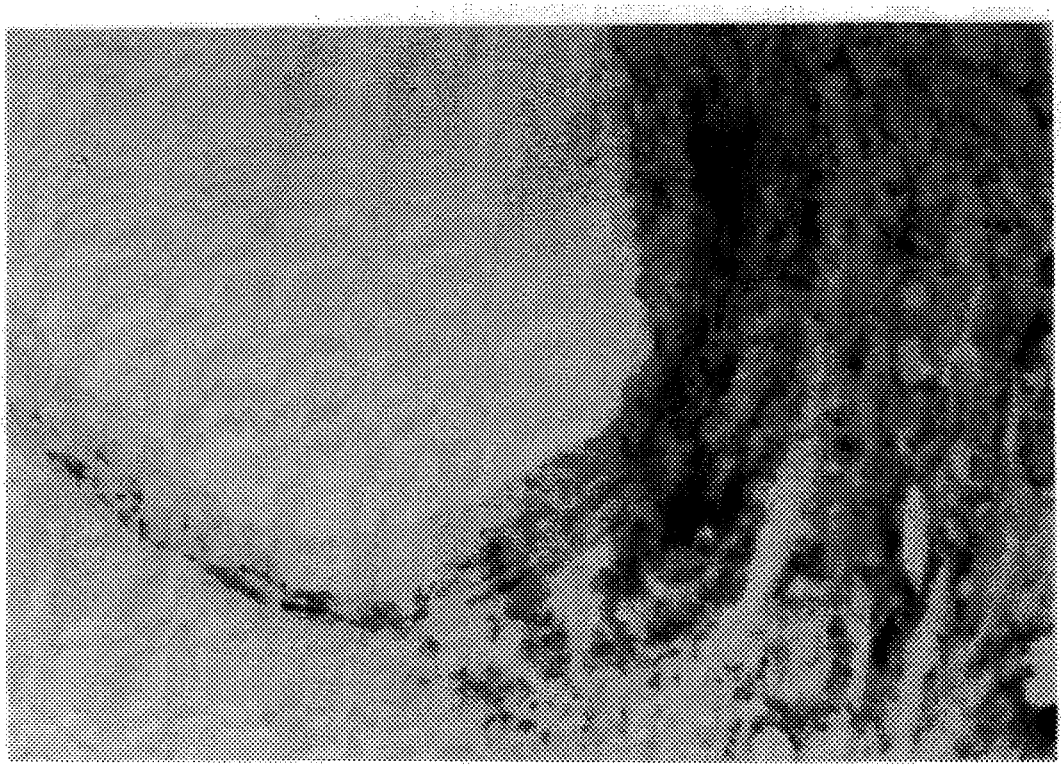
FIG. 9A and 9B are photographs of SV40 large T Antigen staining as detected by immunohistochemistry after transfection of denuded rat carotid arteries by HVJ-liposome mediated gene transfer as described in Example 4.
Figure 9B:
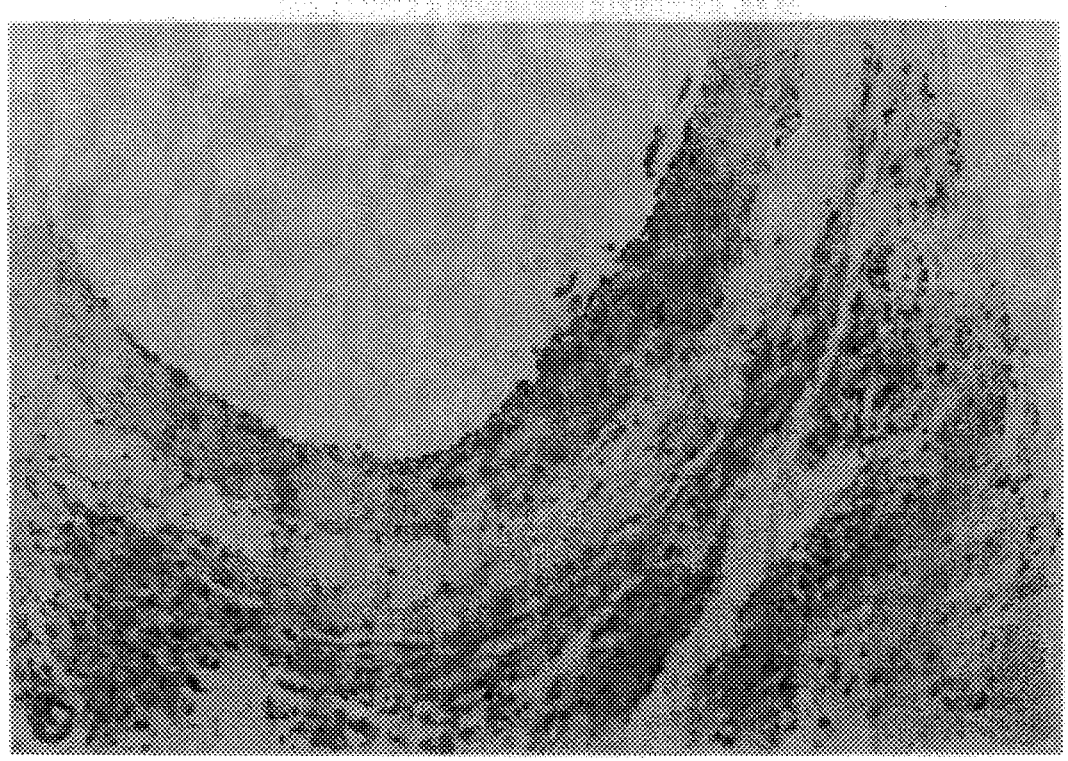
Figure 10A:
FIG. 10A and 10B are photographs of SV40 large T Antigen staining as detected by immunohistochemistry after transfection of intact rat carotid arteries by HVJ-liposome mediated gene transfer as described in Example 4.
Figure 10B:
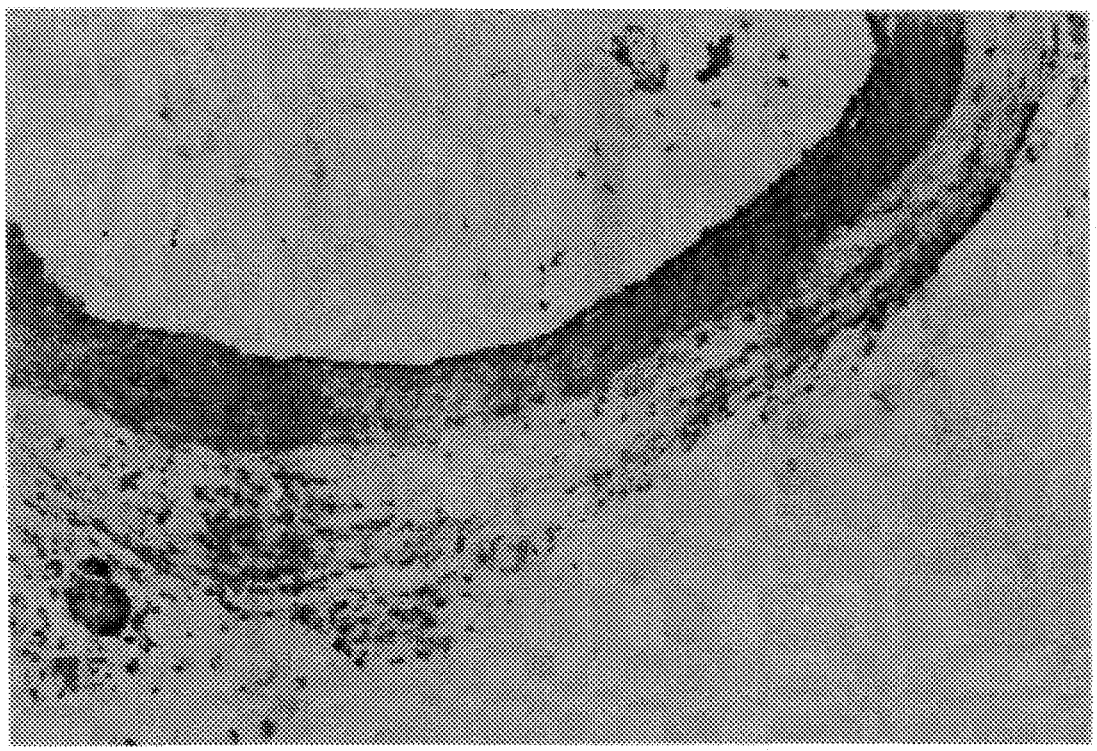

FIG. 9 demonstrates a typical cross-section of SV40 large T antigen transfected blood vessel at 100× magnification after immunohistochemical staining. There is a large amount of staining in the vessel which was denuded prior to transfection with SV40 large T antigen cDNA (FIG. 9A), while the control vector did not result in any staining (FIG. 9B). Of great interest was the unexpected finding that the HVJ-liposome method was so effective in transfecting non-denuded, uninjured blood vessels as shown by FIG. 10A, and that the control transfections showed no staining (FIG. 10B).

Thus, in T antigen gene transfected uninjured as well as injured arteries, the antibody to the gene product protein of transferred SV40 T antigen was seen throughout the layer of the vessels, while no positive staining could be seen in the control-vector transfected vessels. Untransfected arteries also did not show any positive staining using immunoglobin IgG as a control antibody, and there was no nonspecific staining in either transfected or untransfected arteries. The relative amount of SV40 T antigen may show some differences between uninjured and injured vessels. For example, with the injured arteries, wider area of staining (30% or more of medial area) and more intense staining were seen as compared to the uninjured arteries (10% or less of medial area). The SV40 T antigen staining could be readily detected up to 2 weeks after transfection. Using RT-PCR, PCR, SV40 T antigen DNA could also be detected in SV40 transfected vessels 1 week later but not in control vessels. This is the first demonstration of successful in vivo gene transfer into blood vessels after angioplasty injury. The frequency of uninjured versus injured vessels exhibiting SV40 T antigen positive staining 1 week after transfection was examined using observers who are blinded from the protocol. In these experiments, over 80% (9 of 11) of T antigen gene transfected arteries showed positive staining in the injured vessels, and over 60% (7 of 11) of T antigen gene transfected arteries showed in the uninjured vessels. None of the untransfected (4 injured) or the control vector transfected arteries (5 uninjured and 5 injured) showed staining in either uninjured or injured vessels.

It was of interest that the expression of the transgene could be detected in all layers of the vessel wall, especially the media. These observations suggest that the HVJ-liposomes can readily penetrate and/or be transported through different cell layers. The concentration of gene product in the media may reflect the time or pressure of gene transfer in vivo, the increased efficiency in proliferating smooth muscle cells (especially in injured vessel) or a predilection of HVJ-liposomes for smooth muscle cells. The lack of detectable staining of T antigen in the neointimal at 1 week after transfection and injury may reflect an effect of gene dosage per cell as a result of cell replication.

In summary, the HVJ-liposome method is a highly efficient in vivo gene transfer method for blood vessels via intraluminary delivery using the HVJ-liposome method. The widespread expression of the transfected gene in both injured and uninjured vessels supports the usefulness of this method in introducing nucleic acids, e.g. antisense oligonucleotides or plasmid, into many cells to block proliferation or migration that contribute to restenosis or to treat other indications. For example, genes may be transfected whose product can be secreted into the vessel wall where that product exerts a paracrine inhibitory effect on smooth muscle cells, for example, nitric oxide synthase or soluble growth factor receptors.

EXAMPLE 5

Transfer of Antisense Oligonucleotides via HVJ-liposomes

1) In Vitro Transfer of Antisense Oligonucleotides for Cellular Growth Factors for Modification of Cell Growth In order to effectively treat any number of vascular conditions, the transfer of antisense oligonucleotides designed to inhibit or abolish the expression of selected growth related genes would be a means of intervention for example, to treat neointimal hyperplasia as in restenosis.

The pathophysiology of neointimal hyperplasia is complex and involves multiple biologically active mediators and modulators including thrombin, PDGF, bFGF, and angiogenin, etc. For example, factors such as FGF and PDGF stimulate smooth muscle cell proliferation and migration, which is a central event in restenosis (Powell, et al., 1989, Science 245: 186–188; Majesky, et al., 1991, J. Clin. Invest. 88: 904–910; Gercek, et al., 1990, Circ. Res. 66: 1755–1760; Edelman, et al., 1992, J. Clin. Invest. 89: 465–473; and Ling, et al., 1992, Circulation 86: 1–226). Because of the multiplicity of factors involved, strategies that inhibit specifically one or two of the factors may fail. These multiple pathways must converge at G1/S boundary and therefore may share a common mechanism that causes DNA replication. Blocking this common pathway may prevent SMC proliferation after angioplasty regardless multiplicity of factors activated. The serine-threonine protein kinase p34$^{cdc2}$, the product of cdc 2 gene, plays a key role in the regulation of the eukaryotic cell cycle (Arion, et al., 1988, Cell 55:371; Gauter, et al., 1988, ibid 53: 433; Labbe, et al., 1988, Nature 335:251) . PCNA (proliferating cell nuclear antigen: PCNA) is also known to be a nuclear protein required for leading strand DNA synthesis by DNA polymerase delta, which is essential pathway for DNA replication (Prelich, et al., 1988, Cell, 53:117; Giarard, et al., 1991, Cell, 67:1169). These two cell cycle related genes are reported to be coupled and play an important role in cell cycle (Minshull, et al., 1989, Cell, 56:947; Dratta, et al., 1989, Cell, 56:829–838; Labbe, et al., 1989, EMBO J., 8:3053–3058). In order to demonstrate the use of HVJ-liposomes to deliver an effective amount of an antisense therapeutic agent into cells of the vasculature, conditions were first established in vitro. Then, the antisense oligonucleotides were encapsulated in HVJ-liposomes for in vivo intraluminal transfer.

Cell Cultures

RASM cells (passage 4–10) were isolated, cultured and maintained as described in Example 1. In these experiments, cells were plated into 24-well culture dishes at $1\times10^4$ cells/well. After about 80% confluence, the cells were made quiescent by incubation for 48 hours in a defined serum-free medium containing insulin ($5\times10^{-7}$M), transferrin (5 µg/ml), and ascorbate (0.2 mM) as described in Example 2. This growth condition maintains smooth muscle cells in a quiescent, non-catabolic state that promotes the expression of smooth muscle cell-specific contractile proteins.

Preparation of Oligonucleotides

Oligonucleotide sequences utilized in these experiments and their relationships to TGF-$\beta_1$, bFGF, PDGF chain, cdc2 kinase, cdk2 kinase, PCNA and B mRNAs, ind ACE mRNAs (Sporn, et al., 1987, J. Cell Biol. 105:1039–1045; Burgess and Maciag, 1989, Ann. Rev. Biochem. 58:575–606; Betsholz, et al., 1986, Nature 20:695–699; Johnson and Smith, 1991, J. Biol. Chem. 266:402–3407; Lee and Nurse, 1987, Nature 327:31–35; Wang, et 1., 1990, Nature 343:555–557; Lattion, et al., 1989, FEBS Lettrs. 252:99–104) are summarized below (underlined sequences indicate translated sequences).

TABLE I

A. human TGF-$\beta_1$ mRNA [SEQ ID NO: 7]:
5'-GCC UCC CCC <u>AUG CCG CCC UCC GGG</u>-3'
antisense TGF [SEQ ID NO: 8]:
3'-GGG TAC GGC GGG AGG-5'
control sense TGF [SEQ ID NO: 9]:
5'-CCC ATG CCG CCC TCC-3'
control reverse TGF [SEQ ID NO: 10]:
5'-GGG TAC GGC GGG AGG-3'

B. human bFGF mRNA [SEQ ID NO: 11]:
5'-GCA GGG ACC <u>AUG GCA GCC GGG AGC</u>-3'
antisense FGF [SEQ ID NO: 12]:
3'-CCC TGG TAC CGT CGG-5'
control sense FGF [SEQ ID NO: 13]:
5'-GGG ACC ATG GCA GCC-3'
control reverse FGF [SEQ ID NO: 14]:
5'-CCC TGG TAC CGT CGG-3'

C. human PDGF mRNA [SEQ ID NO: 15]:
5'-CGG GAC GCG <u>AUG AGG ACC UUG GCU</u>-3'
antisense PDGF [SEQ ID NO: 16]:
3'-TAC TCC TGG AAC CGA-5'
control sense PDGF [SEQ ID NO: 17]:
5'-ATG AGG ACC TTG GCT-3'

D. murine cdc2 kinase mRNA [SEQ ID NO: 18]:
5'-UGA GUA ACU <u>AUG GAA GAC UAU AUC</u>-3'
antisense cdc2 [SEQ ID NO: 19]:
3'-ACT CAT TGA TAC CTT CTG-5'
control sense cdc2 [SEQ ID NO: 20]:
5'-TGA GTA ACT ATG GAA GAC-3'

E. rat PCNA mRNA [SEQ ID NO: 21]:
5'-AAC UCC GCC ACC AUG UUU GAG GCA CGC CUG-3'
antisense PCNA:1: +4– +21 [SEQ ID NO: 22]:
3'-AAA CTC CGT GCG GAC TAG-5'
antisense PCNA:2: –6– +9 [SEQ ID NO: 23]:
3'-CGG TGG TAC AAA CTC-5'
control sense PCNA 1: +4– +21 [SEQ ID NO: 24]:
5'-TTT GAG GCA CGC CTG ATC-3'
control sense PCNA 2: –6– +9 [SEQ ID NO: 25]:
5'-GCC ACC ATG TTT GAG-3'

F. human CDK2 Kinase mRNA [SEQ ID NO: 26]:
5'-UGG CGC UUC AUG GAG AAC UUC CAA-3'
antisense CDK2 [SEQ ID NO: 27]:
3'-GCG AAG TAC CTC TTG AAG-5'

TABLE I-continued

```
    control sense CDK2 [SEQ ID NO: 28]:
    5'-CGC TTC ATG GAG AAC TTC-3'
G.  rat cyclin B mRNA [SEQ ID NO: 29]:
    5'-GGA GGA GCC AUG GCG CUC AGG GGU-3'
    antisense cyclin B [SEQ ID NO: 30]:
    3'-CCT CGG TAC CGC GAG TCC-5'
    control sense cyclin B [SEQ ID NO: 31]:
    5'-GGA GGC ATG GCG CTC AGG-3'
H.  rat ACE mRNA [SEQ ID NO: 32]:
    5'-ACC GCG CCA UGG GGG C-3'
    antisense ACE [SEQ ID NO: 33]:
    3' T GGC GCG GTA CCC CCG 5'
    control sense ACE [SEQ ID NO: 34]:
    5' ACC GCG CCA TGG GGC C-3'
```

Unmodified, 15-base or 18-base deoxyribonucleotides were synthesized and purified as described in Example 3. In addition or alternatively, phosphorothiate modified oligonucleotides may be synthesized and used to increase nuclease resistance as reported by Agarwal, et al., 1991, Proc. Natl. Acad. Sci. USA 88:7595–7599. Antisense TGF, antisense FGF, antisense PDGF, antisense cdc2, and antisense PCNA oligonucleotides were complementary to human TGF-$\beta_1$ mRNA, bFGF mRNA, and PDGF A chain mRNA, respectively, at the translation initiation region. Antisense cdc2 and antisense PCNA oligonucleotides were complementary to murine cdc2 kinase mRNA and rat PCNA mRNA. Control oligonucleotides were either the sense oligonucleotide (e.g., sense TGF, sense FGF, sense PDGF, sense cdc2, sense PCNA) or the oligonucleotide with the same oligonucleotide sequence but with a reversed 5'-3' orientation (e.g., reverse TGF, reverse FGF).

Preparation of HVJ-Liposomes

HVJ and HVJ-liposomes were prepared as described in Example 1. The lipid mixture of PS, PC and cholesterol in a weight ratio of 1:4.8:2 (10 mg) was deposited on the sides of a flask by removal of the solvent (tetrahydrofuran) in a rotary evaporator. Dried lipid was hydrated in 200 µl of balanced salt solution (BSS) containing the control or antisense oligonucleotides (120 nmol). A further control group was generated using no nucleotides in the procedure (200 µl BSS). The liposome-oligonucleotide complex suspension was prepared by shaking and sonicating the mixture as described in Example 3. Purified HVJ (strain Z) was inactivated by UV irradiation (110 erg/mm$^2$/sec) for 3 minutes immediately prior to use. The liposome suspension (0.5 ml containing 10 mg of lipids) was mixed with the inactivated HVJ (e.g., 10,000–20,000 HAU) in a total volume of 4 ml of BSS. This mixture was incubated a 4° C. for 5 minutes followed by 30 minutes with gentle shaking at 37° C. Free HVJ was then removed from the HVJ-liposomes by sucrose density gradient centrifugation and the top layer of the gradient was collected for use as described in Example 1. The final concentration of oligonucleotides contained in the vesicles was equivalent to about 3 µM. In another experiment, conditions were adjusted to yield vesicles which contained about 15 µM of the oligonucleotides.

Preparation of Cationic Liposomes

Lipofectin® liposomal preparations were done according to the manufacturers protocol as described in Example 2. Briefly, oligonucleotides dissolved in 50 µl defined serum-free (DSF) media were mixed with Lipofectin® reagent (BRL Life Technologies, Gaithersburg, Md.) dissolved in an equal amount of water in a weight ratio of 6:1 (oligonucleotide:Lipofectin®) and incubated for 30 minutes at room temperature.

Transfection Procedures and Materials

After quiescence, cells were washed 3 times with BSS containing 2 mM $CaCl_2$. Then, 500 µl of HVJ-liposomes (1.3 mg of lipids and 3 µM encapsulated oligonucleotides in liposomes) were added to the wells as described in Example I, incubated at 4° C. for 5 minutes and at 37° C. for 30 minutes. The media was changed after incubation to fresh medium with 5% calf serum or DSF, and incubation was overnight at 37° C. in a $CO_2$ incubator. At 3 days after transfection, cells were removed from the plates by trypsinization and counted. Cell counts were compared to determine the effect of transfected antisense oligonucleotides of PCNA alone, of cdc2 kinase alone, and of the combination of PCNA and cdc2 kinase on smooth muscle cell growth.

Determination of DNA Synthesis

Relative rates of DNA synthesis were assessed, as in Example 2, by determination of tritiated thymidine (10 µCi/ml) incorporation into trichloroacetic acid (TCA)-precipitable material as described by (Itoh, et al., 1990, J. Clin. Invest. 86:1690–1697.

Bioassay for bFGF

Extraction of bFGF from RASM cells and bioassay for bFGF activity using murine 3T3 fibroblasts are performed as described by Klagsbrun, et al., 1986, Proc. Natl. Acad. Sci. USA 83:2448–2452. Confluent quiescent RASM cells (1.3× $10^{-7}$) with or without previous treatment with antisense FGF-oligonucleotides are harvested from monolayer cultures by trypsinization washed with PBS, 4 µM pepstatin and 1 mM phenylmethylsulfonyl fluoride. After the cells are disrupted by 3 cycles of freezing and thawing followed by sonication for 1 minute, the homogenate is centrifuged at 25,000 g for 30 minutes and the supernatant was dialyzed overnight against 0.1M NaCl/0.01M Tris-HCl, pH 7.5 (4° C.). The measurement of bFGF activity was made in relation to human bFGF standards (0.03–3 ng/ml, Genzyme Corp., Boston, Mass.) or samples were pre-incubated with either anti-bFGF IgG (R&D Systems, Minneapolis, Mn.) or non-immune IgG at 10 µg/ml with quiescent Swiss 3T3 cells for 20 hours, after which the cells were pulse-labeled with 10 µCi/ml $^3$H-thymidine for 8 hours. Serial dilution curves of all extracts (parallel to the standard bFGF curve) are established to estimate cellular bFGF content by antibody suppressible mitogenic activity in the samples.

Results

The in vitro transfer of antisense FGF [SEQ ID NO:12], TGFβ [SEQ ID NO:8], and PDGF [SEQ ID NO:16]to cultured RASM cells resulted in inhibition of cell proliferation as measured by tritiated thymidine incorporation by the methods described in Example 1. The transfer of antisense FGF [SEQ ID NO:12] resulted in a 70% reduction in thymidine incorporation by endothelial cells, and a 15% reduction in incorporation by smooth muscle cells. The transfer of antisense TGF-β [SEQ ID NO:8] resulted in a 35% increase in the thymidine incorporation of RASM cells, suggesting that TGF-β plays a role in inhibiting VSMC growth. The transfer of antisense PDGF [SEQ ID NO:16] resulted in a modest 10% reduction of VSMC thymidine incorporation. Taken together, these results illustrate the effective use of HVJ-liposome mediated transfer to alter the growth characteristics of vascular cells.

Figure 11:
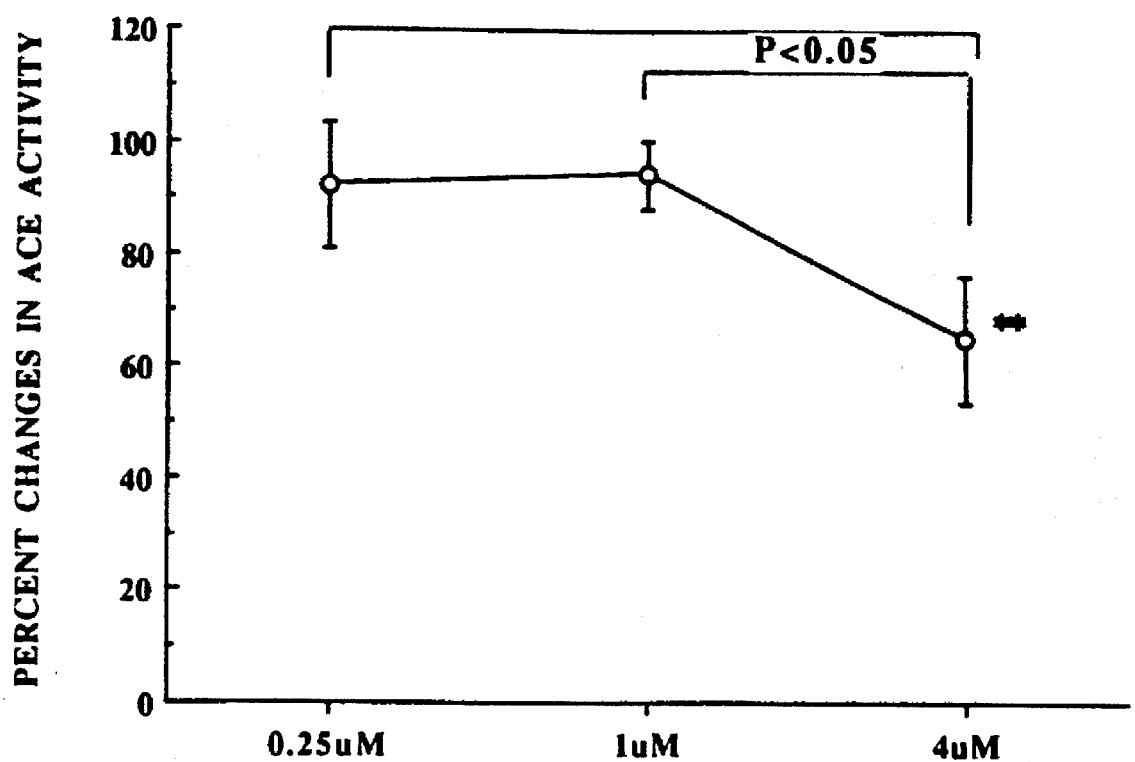
FIG. 11 is a graph illustrating the dose effect of antisense ACE (open circles) on ACE activity in VSMC in culture as measured by an ACE bioassay as described in Example 1.

In vitro administration of antisense ACE via HVJ-liposome mediated transfer resulted in a significant decrease in ACE activity as compared to that of control sense ACE treatment as illustrated in FIG. 11 in a dose dependent fashion.

2) Increased Effectiveness of Antisense Oligonucleotide Treatment via HVJ-liposome Transfection: Cotransfection With Non-Histone Nuclear Proteins and Enzymes In order to test the transfection of antisense ACE and the effect of HMG1 and RNase H on the inhibition of ACE activity, RASM cells isolated from 2 week old WKY rats were transfected with the antisense HVJ-liposomes. The ACE activity of the cells was measured by hippuryl-L-histidyl-L-leucine (HHL) hydrolysis as described in Example 1.

Results

Figure 12:
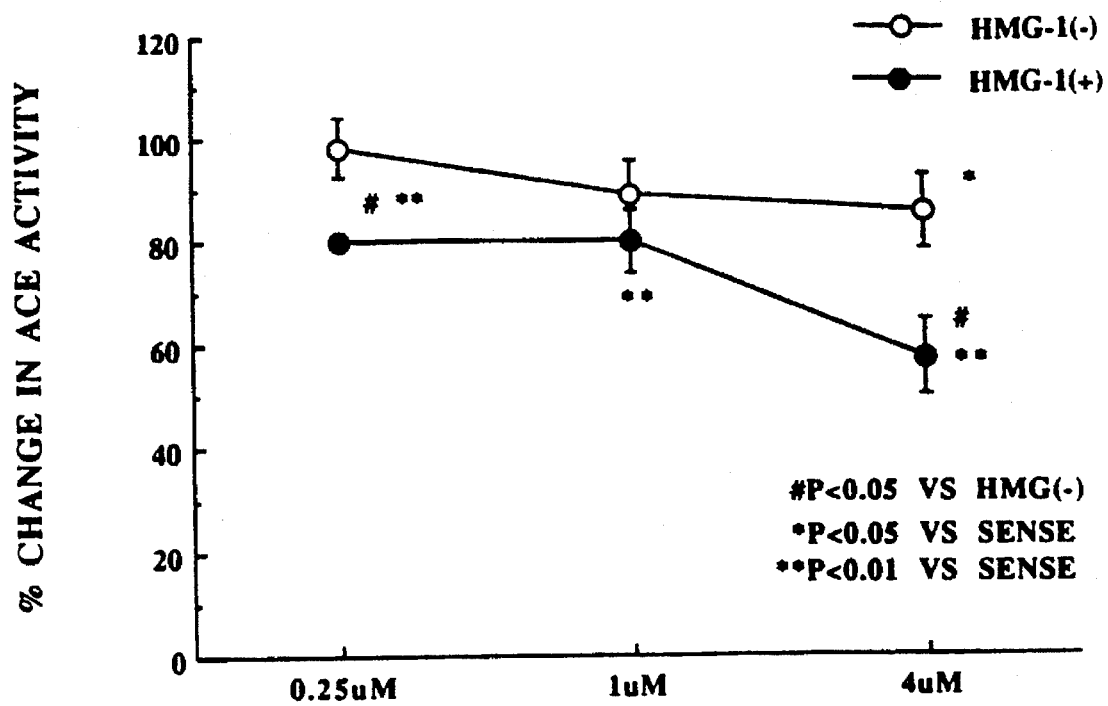
FIG. 12 is a graph illustrating the effect of HMG1 on ACE activity in VSMC via HVJ-liposome transfection of antisense ACE oligonucleotides, measured as percent change in ACE activity with antisense versus sense, with sense considered to be 100% (open circles—no HMG1; closed circles—with HMG1).
Figure 13:
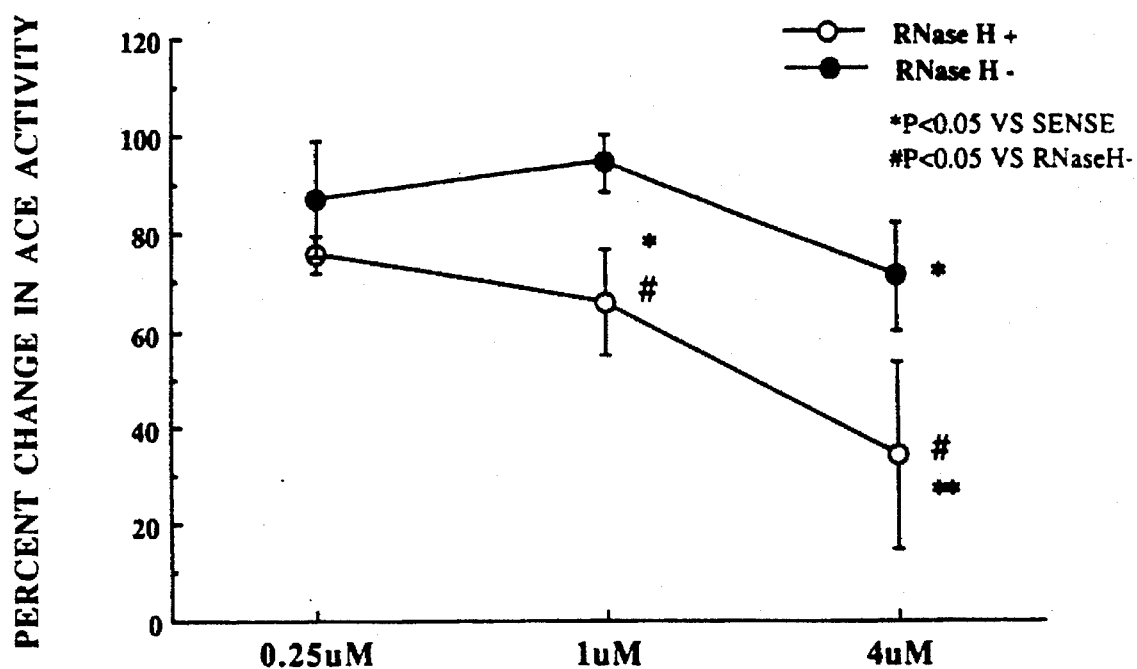
FIG. 13 is a graph illustrating the effect of antisense ACE with or without RNase H (50 U) on ACE activity of VSMC after transfection via HVJ-liposomes, measured as percent change in ACE activity with antisense versus sense, with sense considered to be 100% (open circles—with RNase H; closed circles—no RNase H).
Figure 14:
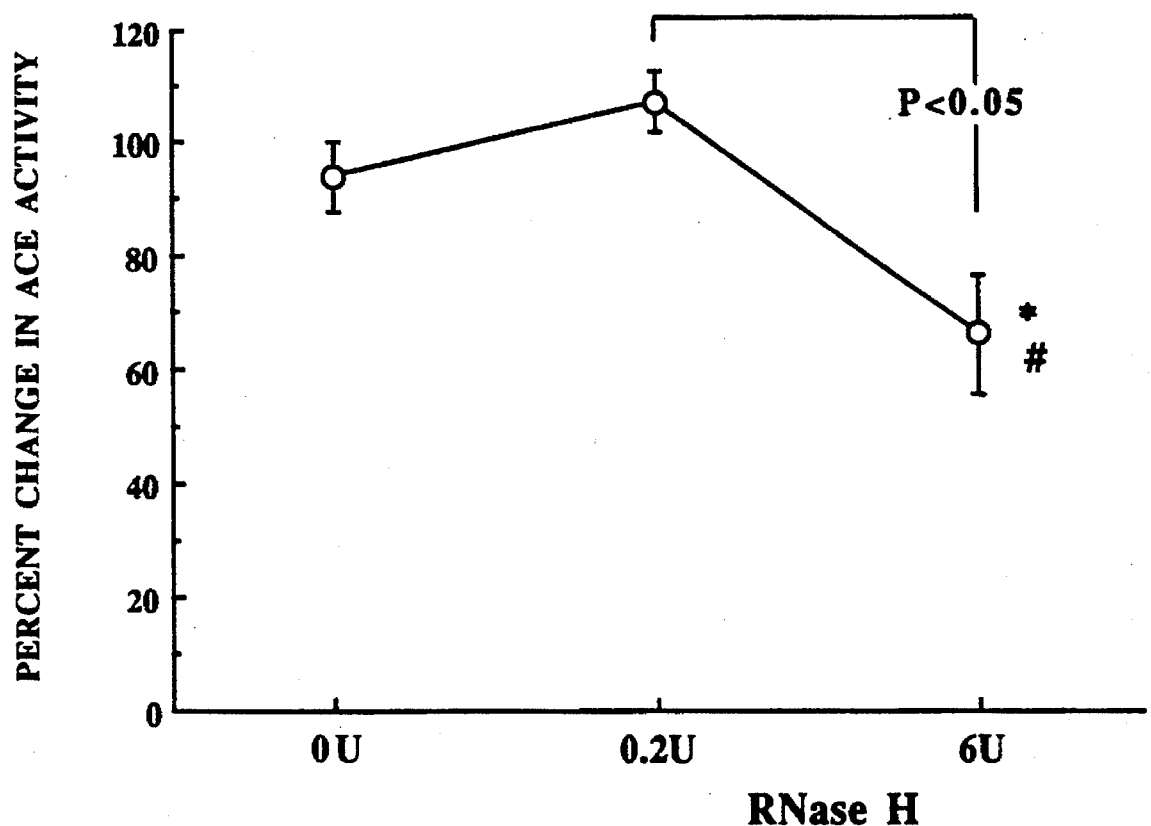
FIG. 14 is a bar graph illustrating the dose effect of the addition of RNase H to antisense ACE (1.0 µM) measured as percent change in ACE activity with antisense versus sense, with sense considered to be 100%, after transfection via HVJ-liposomes, as compared with transfection of sense oligonucleotide.

The in vitro administration of antisense ACE [SEQ ID NO:33] in combination with non-histone nuclear protein (HMG1) is illustrated in FIG. 12. The results indicate that the effect of cotransfection of antisense oligonucleotides with HMG1 as measured by decrease in ACE activity as compared with control sense ACE transfection, was consistently better than antisense oligonucleotides without HMG1. The effect of cotransfection of 50 U of RNase H with varying concentrations of antisense oligonucleotides is illustrated in FIG. 13. As compared with the ACE activity of control transformations without RNase H, the addition of RNase H increased the effectiveness of the antisense treatment. Examination of the dose effect of RNase H when transfected with a constant 1 μM of antisense AGE is illustrated in FIG. 14. At 50 U of RNase H, a dramatic increase in effectiveness of the antisense treatment is seen.

3) In Vivo Transfer of Antisense Oligonucleotides for Cell Cycle Genes for the Inhibition of Neointimal Hyperplasia and Smooth Muscle Cell Proliferation Procedure for In Vivo Transfer and Assays Endothelial denudation and vascular injury in the left common carotid artery of 4 month-old male rats (Sprague-Dawley, 450–500 g) was achieved by passing a number 2 French Fogarty balloon catheter (Baxter, Calif.) through the external carotid into the aorta. The balloon was then inflated to 2 atm to distend the common carotid and was then pulled back to the external carotid three times (Clowes, et al., 1985, Lab. Invest. 49:208; Clowes and Schwartz, 1985, Cir. Res. 56:139). After angioplasty, the injured segment of the common carotid was transiently isolated by the temporary ligation of both ends. The vessel segment was flushed with heparin-PBS to remove blood and the HVJ-liposome-AS complexes (about 3 μM oligonucleotides entrapped) were introduced into the segment and incubated for 15 minutes at room temperature. Immediately after incubation, the external carotid segment was ligated upon withdrawal of the catheter, then blood flow in the common carotid was restored by removal of the two temporary ligatures on the common carotid and the wound closed. To determine the effect of the oligonucleotides transferred on DNA synthesis in the injured vessel, the animals were injected with BrdU (bromodeoxyuridine). BrdU is a thymidine analog incorporated into newly synthesized DNA and is detected immunohistochemically.

After transfection via HVJ-liposomes, the carotid arteries were removed 4 days later, fixed in 4% paraformaldehyde, and processed for histology using standard procedures. Representative cross-sections of rat carotid arteries from untreated, antisense treated and sense treated animals were stained and compared as described previously using computer assisted morphometry. Evidence of neointimal hyperplasia can be demonstrated by showing the thickening of the neointimal layer as compared with the unaffected medial layer. Using the cross-sectional areas of the neointima and the medial layer, it is possible to arrive at a ratio comparing the two measurements, the neointimal:medial ratio. Intimal and medial areas were measured using a digitizing tablet (Southern Micro Instruments, model 2200, Atlanta, Ga.).

Results

The in vivo transfer of antisense cdc2 kinase [SEQ ID NO:19] and antisense PCNA [SEQ ID NO:22] reduced cell proliferation and neointima formation after balloon angioplasty injury. Rat carotid arteries that were denuded and incubated with the HVJ-liposome complex containing antisense cdc2 [SEQ ID NO: 19] and antisense PCNA [SEQ ID NO:22] within the lumen of the treated segment for only 10–15 minutes at room temperature showed no signs of neointima hyperplasia as compared with controls.

Figure 15:
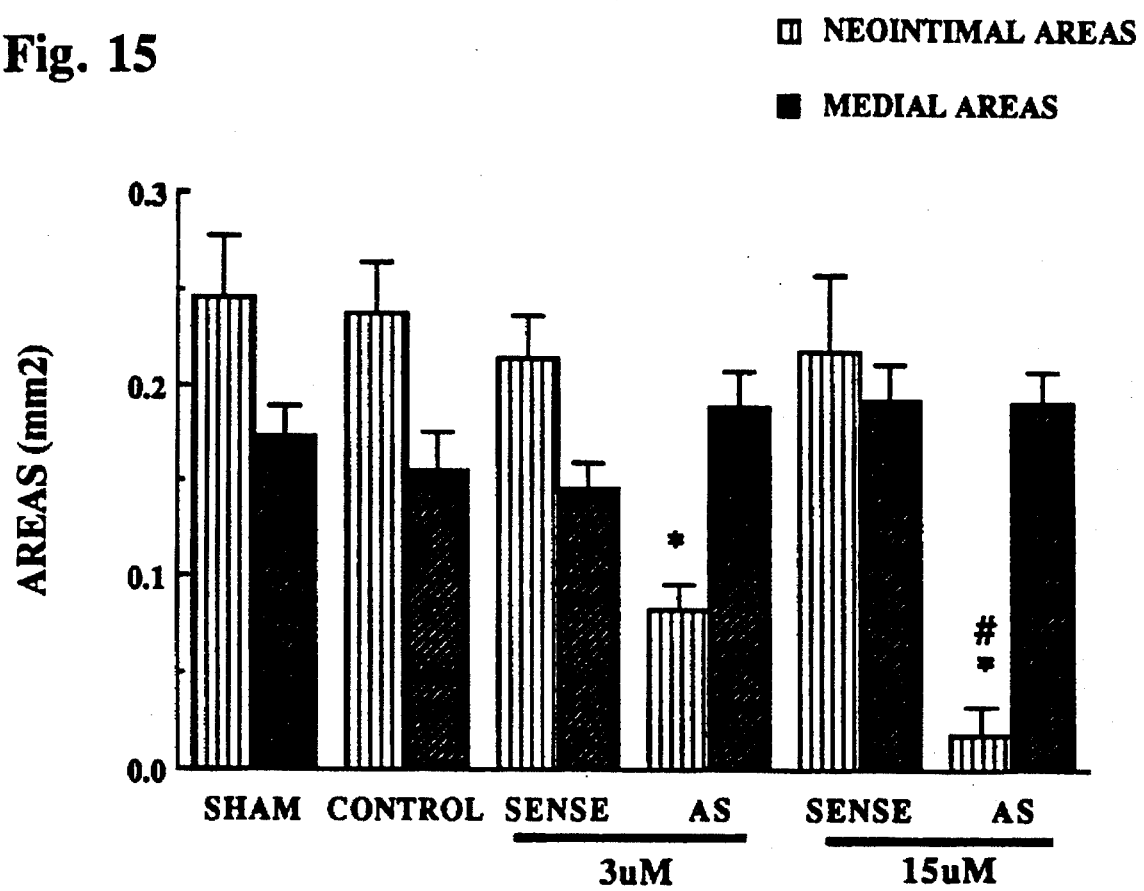
FIG. 15 is a graph illustrating the effect of HVJ-liposome transfection of antisense cdc2 and antisense cyclin A into intact carotid arteries in vivo for the prevention of hyperplasia as described in Example 5. Hyperplasia is measured as the formation of neointima apparent as an increase in the relative neointima/medial layer ratio of a cross section of a treated blood vessel (open circle 3 µM; closed circle 15 µM).
Figure 16:
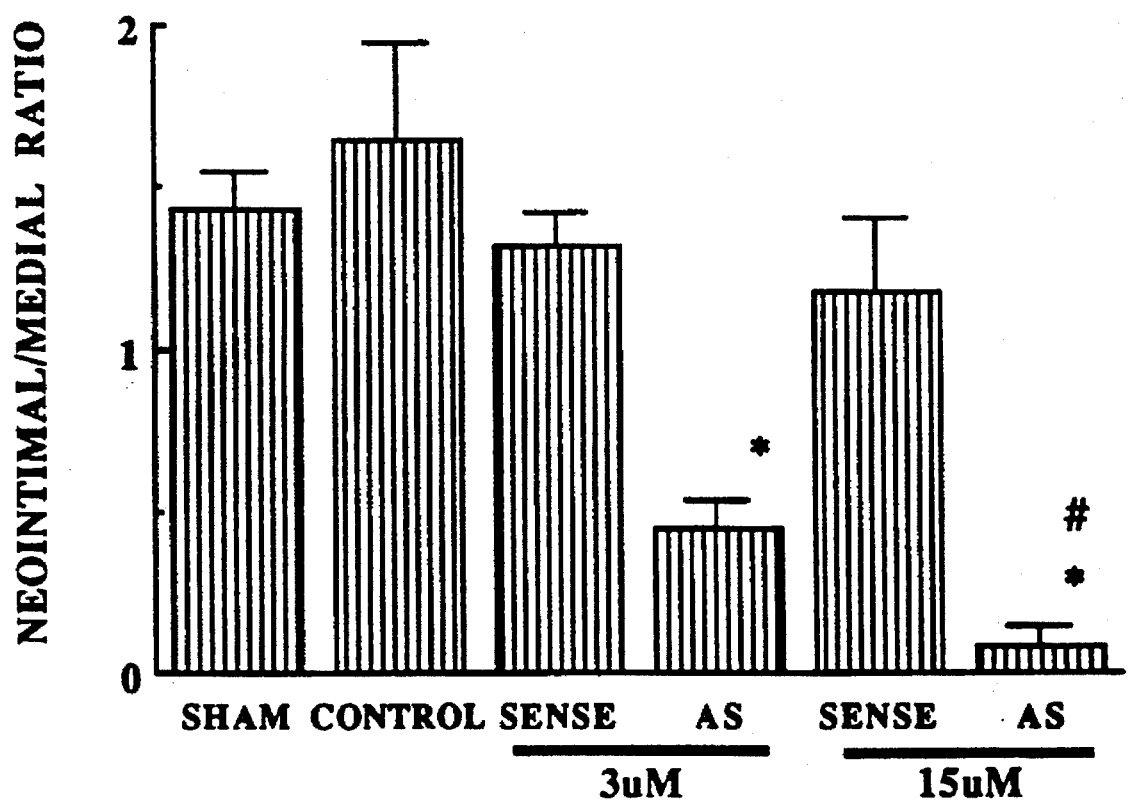
FIG. 16 is a bar graph illustrating the inhibition of hyperplasia as measured by the inhibition of neointima formation as described in Example 5. The measured area of the medial layer of examined cross-sections, showing changes in the neointimal/medial ratio due primarily to differences in the neointima is shown.
Figure 17A:
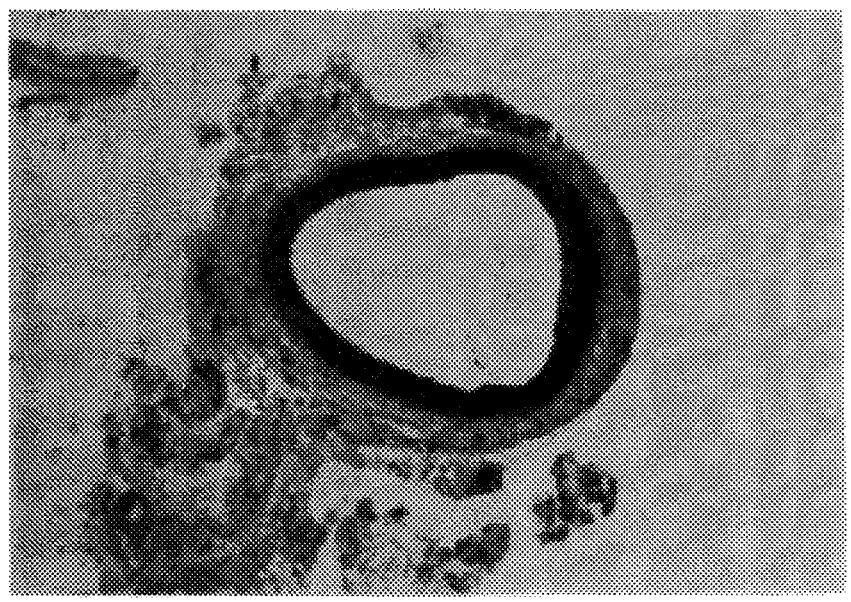
FIG. 17 is photographs of cross-sections of carotid arteries stained for elastin to reveal the medial and intimal tissue layers. The uninjured control vessel is a normal carotid artery. The injured control vessel is a carotid artery which has been damaged via balloon angioplasty and not given treatment. The injured sense vessel is a carotid artery which has been damaged via balloon angioplasty and treated with sense-oligonucleotides as described in Example 5 and which shows thick neotimal formation. The injured antisense vessel is a carotid artery which has been damaged via balloon angioplasty, and treated with antisense oligonucleotides determined by HVJ-liposome treatment as described in Example 5 and which shows little or no neointimal formation.
Figure 17B:
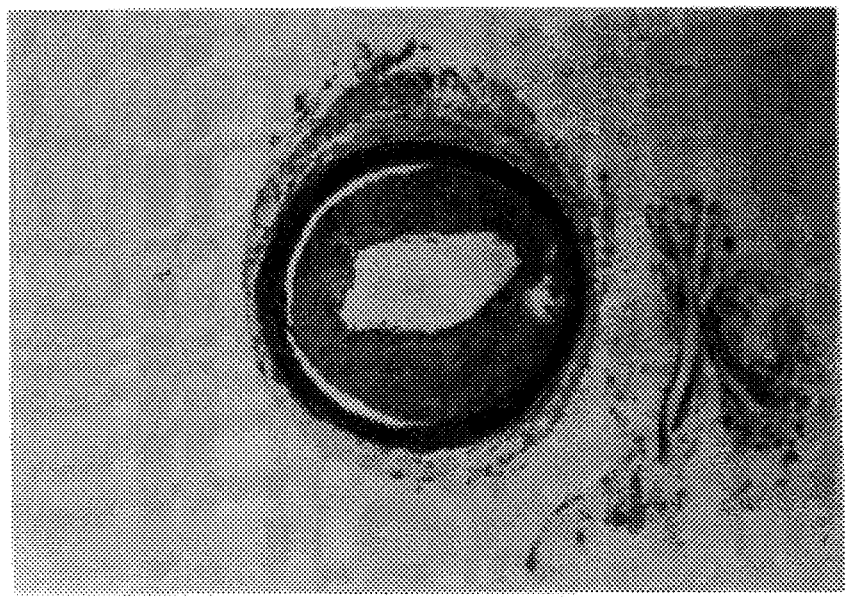
Figure 17C:
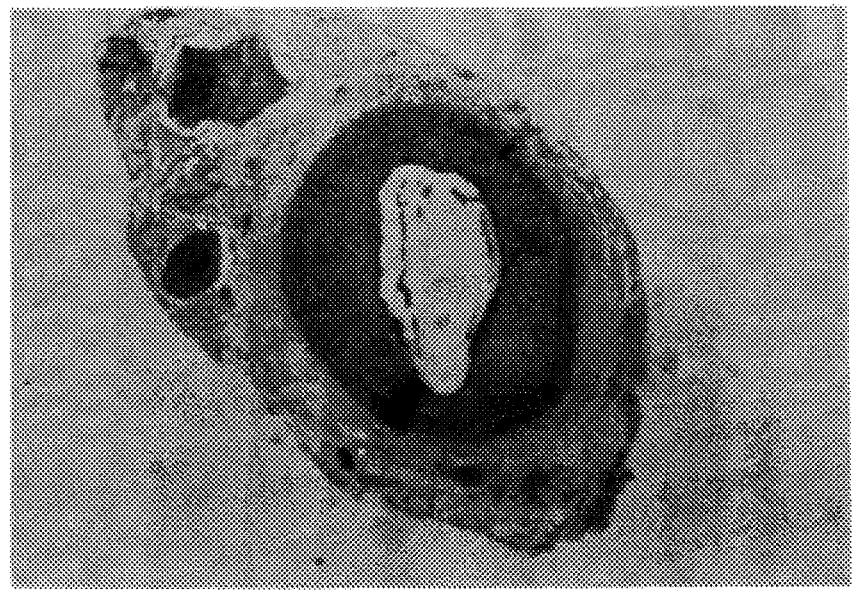
Figure 17D:
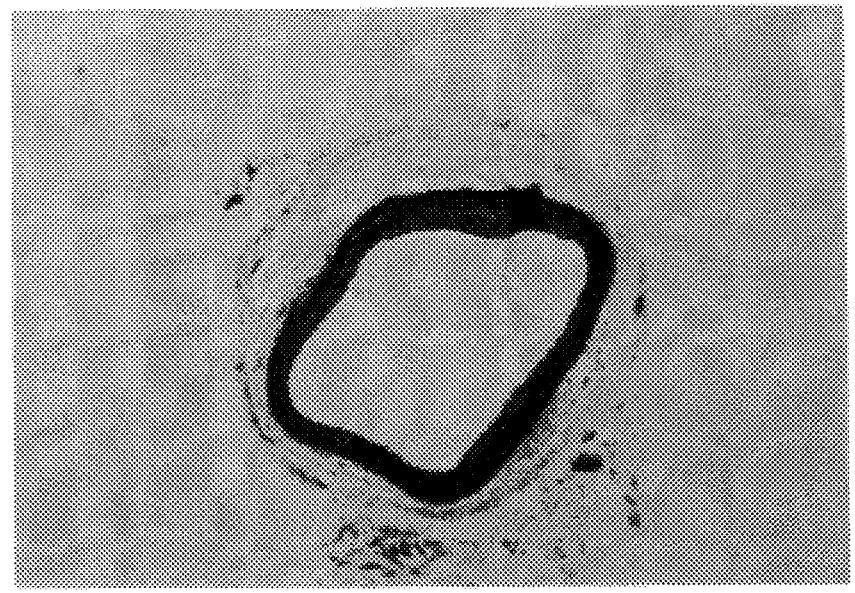

Examination of the effect of antisense cdc2 [SEQ ID NO:19] and antisense PCNA [SEQ ID NO:22] on the area ($mm^2$) of the neointima as a ratio of the area ($mm^2$) of the medial zone revealed that the antisense treatment was highly effective at 3 μM, and even more effective at 15 μM, in preventing the proliferation and hyperplasia of the neointima. FIG. 15 compares the results for transfection with control empty vesicles, sense cdc2 [SEQ ID NO:18] and PCNA [SEQ ID NO:21], and antisense cdc2 [SEQ ID NO:18] and PCNA [SEQ ID NO:22]. An increase in the effectiveness of the antisense treatment over that of the sense oligonucleotides was demonstrated. An increase in effectiveness was also demonstrated when the antisense oligonucleotide concentration was increased from 3 μM to 15 μM. A comparison of the ratio derived from the neointimal:medial areas with the measured medial areas ($mm^2$) as shown in FIG. 16, illustrates that the difference in the ratio is due to changes in the thickness of the neointima, and not due to changes in the medial layer. FIG. 17 shows crosssections of carotid arteries stained for elastin (Sigma Chemical Co., St. Louis, Mo.) to reveal the medial and intimal tissue layers. The uninjured control vessel shown is a normal carotid artery. The injured control vessel shown is a carotid artery which has been damaged via balloon angioplasty and not given treatment. The injured sense vessel shown is a carotid artery which has been damaged via balloon angioplasty and treated with sense oligonucleotides as described in Example 5 and which shows thick neointimal formation. The injured antisense vessel shown is a carotid artery which has been damaged via balloon angioplasty, and treated with antisense oligonucleotides in accordance with the HVJ-liposome treatment as described in Example 5 and which shows little or no neointimal formation.

Further measurements of cellular activity were done at 4 days after transfection. Carotid arteries treated with antisense cdc2 and PCNA showed a significantly lower DNA synthesis rate compared to control and sense oligonucleotide treatments as measured by BrDU uptake assay. The effect of the oligonucleotides transferred on DNA synthesis in the injured vessel was determined by infection of the animals with BrdU (bromodeoxyuridine) as shown in Table 2.

TABLE 2

| Control | 21 ± 3% | BrdU labeling |
| --- | --- | --- |
| Sense | 23 ± 3% | BrdU labeling |
| Antisense | 10 ± 1% | BrdU labeling |

In addition, total vessel DNA content was lower in the antisense groups than control groups. This treatment was effective for up to 2 weeks after transfection. HVJ-liposome transfection enhanced the stability of the oligonucleotides for 72 hours, comparable to the stability of phosphorothiate nucleotides for the generation of an AS-oligonucleotide. The combination of phosphorothioate AS-oligonucleotides and the use of HVJ-liposome methodology increased the effectiveness of the treatment to at least 2 weeks.

In these experiments, the use of antisense oligonucleotides via HVJ-liposome transfer was demonstrated to block the synthesis of various growth factors and cell cycle proteins both in vitro and in vivo. In vivo, the result of such oligonucleotide transfer was inhibition of neointimal hyperplasia. Short-term luminal delivery of antisense oligomers (e.g., cdc2 kinase and PCNA) via HVJ-liposomes was able to prevent lesion formation, i.e., myointimal hyperplasia after vascular injury, and thus is useful for prevention of restenosis after angioplasty. To further increase the effectiveness of the antisense treatment, HVJ-liposome mediated transfection was studied using the ACE system of Example 1. The ACE system is believed to play a role in the SMC hypertrophy that accompanies hypertension, thus selective inhibition of targeted cells of the vasculature would provide an effective means of treating damage to vessels due to hypertension. Cells expressing ACE were subjected to HVJ-liposome mediated transfection of antisense ACE, antisense ACE combined with HMG1, and antisense ACE combined with RNase H. The results from these experiments indicated that the efficiency of HVJ-liposome transfection of antisense ACE is improved by the use of non-histone nuclear proteins, as measured by decrease in ACE activity as compared to control sense ACE transfection. It was further determined that increasing amounts of RNase H cotransfected with antisense ACE by HVJ-liposomes improves the effectiveness of the antisense treatment in a dose dependent manner. Thus the combined use of antisense oligonucleotides, HMG1, and enzymes such as RNase H, all transfected via HVJ-liposomes, would act as an effective therapeutic strategy for the inhibition of gene expression in target cells.

EXAMPLE 6

Preparation of Liposomes Comprising Luminal Compositions in High Concentration (1) Preparation of HVJ-containing liposomes.

A mixture of 250 mg of egg yolk phosphatidyl choline and 33 mg of cholesterol in chloroform and methanol (9:1) was lyophilized in the presence of nitrogen gas.

Isolated F and HN polypeptide (6 mg and 3 mg, respectively) were mixed with 20 mg of lyophilized lipids in 0.85% NP-40 and the liposomes were formed by dialysis against BSS (buffered salt saline) (for six days to remove the detergent). Uchida et al., J. Cell. Biol. 80, 10 (1979). Liposomes with fusion proteins were separated from unincorporated proteins by Bio Gel A50m (BioRad) gel filtration. Liposomes with spikes were eluted in the void fraction. HAU (hemagglutinating unit) of the liposomes was calculated by measuring optical density (OD) at 540 nm. 1 OD at 540 nm corresponded to about 6,000 HAU, which correlated with fusion activity. The purified liposomes contain spikes of HVJ on the envelope and can be stored at 4° C. for a week.

(2) Preparation of liposomes comprising luminal compositions.

The procedure employed is substantially described by Kato et al., J. Biol. Chem. 266, 3361 (1991). 10 mg phosphatidyl serine, 20 mg cholesterol and 48 mg phosphatidyl choline was solubilized in tetrahydrofuran (3.9 ml). 0.5 ml alliquots (10 mg lipid mixture) were made in glass tubes and evaporated in a rotary evaporator at 45° C. for 20 min. in vacuo at 400 mm Hg. The dried lipids were stored at −20° C. under nitrogen for 1–2 weeks. 200 µg plasmid DNA and 64 µg HMG-1 in 0.2 ml BSS were added to the lipids and agitated intensely by vortexing for 30 sec. The tube was allowed to stand in a 37° C. water bath for 30 sec. The vortexing-incubation cycle was repeated eight times. The glass tube was then sonicated for 3–5 sec. in a bath-type sonicator and agitated for 30 sec. by vortexing. 0.3 ml of BSS was added to the tube containing the liposome solution followed by incubation for 30 min. with shaking in a water bath shaker. The tube was then left on ice. It was found that plasmid DNA up to 20 kbp could be enclosed in the lumen at a ratio of 10–30% of initial amounts. Efforts to prepare the liposomes with high molecular weight DNA and include the F and HN proteins in the membrane were unsuccessful.

(3) Preparation of fusion liposomes.

Liposomes with HVJ spikes (F and HN) corresponding to 9,000 HAU were mixed in TE with the liposomes containing DNA and HMG-1 prepared as described above. The mixture was incubated at 4° C. for 10 min. and at 37° C. for 30 min. with shaking. After that, the preparation was separated by sucrose gradient centrifugation. 10-20-30% (w/v) step gradient of sucrose solution in BSS was prepared and the liposome mixture was added to the gradient and centrifuged for 3 hr. at 62,800 G at 4° C. The fusion particles constructed from the two liposomes sedimented in a layer between 10–20%. The fusion particles were collected and stored at 4° C.

Results

Using the above procedure, 200 micrograms of [20 mer] FITC-oligonucleotides (ODN) were trapped in liposomes (10 mg lipids) by vortexing and sonication. These liposomes were then fused with the liposomes with HVJ spikes (9,000 HAU) and the resulting fusion particles purified by sucrose gradient centrifugation. The fusion particles were incubated with mouse L-cells (1–10 million cells) a mouse fibroblast cell line, in suspension (1 ml of DMEM with $10^{-1}$ TES) at 4° C. at 5 min. and then at 37° C. for 30 min. with shaking. After that, cells were observed under fluorescence microscopy. Fluorescence was seen in the nuclei of all the L-cells, while no fluorescence was detected in L-cells, either treated with fusion particles with FITC-ODN or treated with liposomes containing FITC-ODN without liposomes having HVJ spikes. When an expression construct comprising bacterial β-galactosidase gene driven by the chick β-actin promoter was introduced into mouse L-cells or human FL cells using the procedure described above, the transient expression of the transgenic cells was almost 100%. The bacterial β-galactosidase gene construct was also successfully introduced into rat liver by fusion particles and the expression of β-galactosidase was observed in 10–20% of the liver cells, when the particles were injected into the portal vein as described in the procedure by Kaneda et al., J. Biol. Chem., 1989, supra.

The above results demonstrate that one can efficiently transfer to cells under a wide variety of conditions a spectrum of different agents. Even high molecular weight compounds, such as nucleic acids may be efficiently introduced. In this manner, one can provide for transient or permanent modification of cells, with changes in phenotype, so as to provide for varying capabilities of the cell. In addition, the subject methodologies and compositions may be used for prophylaxis or therapy, in the treatment of a wide variety of indications, particularly associated with cellular proliferation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for producing liposomes for fusion with cells, said method comprising:
   agitating in a first aqueous medium purified HN and F proteins of Sendai virus with liposome forming lipids to form first liposomes;
   agitating in a second aqueous medium an agent of interest with liposome forming lipids to form second liposomes,
   wherein at least 25 mole % of the total lipids is cationic lipids;
   combining said first and second liposomes under fusing conditions to provide liposomes for fusion with cells.

2. A method according to claim 1, wherein said first aqueous medium comprises from about 0.1–2% of a non-ionic detergent.

3. A method according to claim 1, wherein said total lipids comprises from about 5 to 20 mole % of cholesterol.

4. A method according to claim 1, wherein said cationic lipids comprise phosphatidyl choline.

5. A method according to claim 1 wherein the weight ratio of first and second liposomes to form the liposomes for fusion are in a weight ratio of 1:1–5 and said Sendai virus is the Z strain of the hemagglutinating virus of Japan (HVJ).

6. A method for producing liposomes for fusion with cells, said method comprising:
   agitating in a first aqueous medium purified HN and F with liposome forming lipids to form first liposomes;
   agitating in a second aqueous medium nucleic acids and a high mobility group protein with liposome forming lipids to form second liposomes,
   wherein at least 25 mole % of the total lipids is cationic lipids;
   combining said first and second liposomes under fusing conditions to provide liposomes for fusion with cells.

7. A method according to claim 6, wherein said first aqueous medium comprises from about 0.1–2% of a non-ionic detergent.

8. A method according to claim 6, wherein said total lipids comprises from about 5 to 20 mole % of cholesterol.

9. A method according to claim 6, wherein said nucleic acids are antisense molecules of from about 15 to 200 bases.

10. A method according to claim 6, wherein said nucleic acids are an expression cassette comprising regulatory sequences functional in said cell and an open reading frame encoding a transcription product of interest.

* * * * *